(12) United States Patent
Horton

(10) Patent No.: US 8,673,554 B2
(45) Date of Patent: Mar. 18, 2014

(54) MULTIPLEX CELL SIGNALLING ASSAYS

(75) Inventor: Jeffrey K. Horton, Cardiff (GB)

(73) Assignee: Ge Healthcare UK Limited, Little Chalfont (GB)

( * ) Notice: Subject to any disclaimer, the term of this patent is extended or adjusted under 35 U.S.C. 154(b) by 447 days.

(21) Appl. No.: 12/812,744

(22) PCT Filed: Jan. 15, 2009

(86) PCT No.: PCT/EP2009/050427
§ 371 (c)(1),
(2), (4) Date: Jul. 13, 2010

(87) PCT Pub. No.: WO2009/090215
PCT Pub. Date: Jul. 23, 2009

(65) Prior Publication Data
US 2010/0311069 A1   Dec. 9, 2010

(30) Foreign Application Priority Data
Jan. 18, 2008 (GB) .................... 0800938.3

(51) Int. Cl.
*C12Q 1/68* (2006.01)
*G01N 33/53* (2006.01)
*A61K 49/00* (2006.01)

(52) U.S. Cl.
USPC ....... 435/6; 435/3; 435/7.1; 435/7.2; 435/7.6; 435/47; 435/362; 436/34; 436/35; 436/56; 436/63; 424/9.2

(58) Field of Classification Search
USPC ......... 435/3, 6, 7.1, 7.2, 7.6, 172.3, 358, 361, 435/362; 436/56, 63, 34, 35; 935/23; 424/9.2
See application file for complete search history.

(56) References Cited

U.S. PATENT DOCUMENTS

| | | |
|---|---|---|
| 4,683,202 A | 7/1987 | Mullis |
| 6,066,476 A | 5/2000 | Tsien et al. |
| 6,077,707 A | 6/2000 | Tsien et al. |
| 6,172,188 B1 | 1/2001 | Thastrup et al. |
| 6,900,019 B1 | 5/2005 | Horton |
| 2005/0164321 A1 | 7/2005 | Riss et al. |
| 2007/0087344 A1 | 4/2007 | Plavec et al. |

FOREIGN PATENT DOCUMENTS

| | | |
|---|---|---|
| EP | 1 439 384 | 5/2008 |
| WO | WO 98/58074 | 12/1998 |
| WO | WO 01/67103 | 9/2001 |
| WO | WO 01/68922 | 9/2001 |
| WO | WO 2004/022711 | 3/2004 |
| WO | WO 2005/118839 | 12/2005 |

OTHER PUBLICATIONS

Hanson. Multiplexing Fluo-4 NW and a GeneBLAzer® Transcriptional Assay for High-Throughput Screening of G-Protein-Coupled Receptor, Journal of Biomolecular Screening 11 (6): 644-651 (2006).*

Naylor. Reporter Gene Technology: The Future Looks Bright. Biochemical Pharmacology, vol. 58, pp. 749-757, (1999).*

(Continued)

*Primary Examiner* — Gail R Gabel

(57) ABSTRACT

Disclosed are methods useful in multiplex cell-based assays for compound screening employing imaging instrumentation. The methods described herein offer high content information relating to the biological potency of test agents, off-target effects and cellular toxicity of potential drug candidates.

14 Claims, 16 Drawing Sheets

Relationship between NFAT1c translocation & TNFα release from ionomycin+ PMA stimulated U2OS transfected cells

(56) References Cited

OTHER PUBLICATIONS

Bertelsen, M., Methods in Enzymology, (2006), 414, 348-363.
Czerkinsky, C., et al., J. Immunol. Methods, (1983), 65 (1-2), 109-21.
Giuliano, et al., J Biomol Screen., (1997), 2, 249-259.
Grunow, R., et al., J. Immunological Methods, (1994), 171, 93-102.
Howell, B. J., et al., Methods in Enzymology, (2006), 414, 284-300.
Nickischer, D., et al., Methods in Enzymology, (2006), 414, 389-418.
Ugozzoli, et al., Analytical Biochemistry, (2002), 307, 47-53.
Bronstein, et al., Analytical Biochemistry, (1994), 219, 169-181.
Beaucage, S., et al., Tetrahedron Letters, (1981), 22(20):1859-1862.
Bridgewater, J., et al., European Journal of Cancer, (1995), 31A(13/14):2362-2370.
Cormack, B., et al., Gene, (1996), 173:33-38.
De Wit, J., et al., Mutation Research, (1981), 80(1):221-226.
Drucker, L., et al., Blood, (2002), 100(11):366b-367b, Abstract.
Evans, G., et al., Journal of Neuroscience Methods, (2007), 160(2):197-205.
Freshney, R., Cloning and Selection of Specific Cell Types in Culture of Animal Cells, 3rd edition, Wiley-Liss Inc., Chapter 11, pp. 161-178, 1994.
Hanson, B., Journal of Biomolecular Screening, (2006), 11(6):644-651.
Howell, B., et al., Methods in Enzymology, (2006), 414:284-300.
Jonas, J., et al., Diabetes, (1998), 47:1266-1273.
Kohno, D., et al., Diabetes, (2003), 52(4):948-956.
Lundgren, E., et al., World Journal of Surgery, (1996), 20(7):727-735.
Marriott, I., et al., Journal of Cellular Physiology, (1998), 177(2):232-240.
Matthes, H., et al., The EMBO Journal, (1984), 3(4):801-805.
McMillen, M., et al., Critical Care Medicine, (1995), 23(1):34-40.
Naylor, L., Biochemical Pharmacology, (1999), 58:749-757.
Neuss, S., et al., Biomaterials, (2007), 29(3):302-313.
Saiki, R., et al., Science, (1988), 239:487-491.
Sambrook, J. et al., Molecular Cloning—A Laboratory Manual, Cold Spring Harbor Laboratory Press, (1989), pp. 14.5-14.21, 16.30-16.46, 16.56-16.57.
Veronesi, B., et al., Neurotoxicology, (2003), 24(3):463-473.
Yang, P., et al., Neuropharmacology, (2005), 49(3):300-316.
Ye, N., et al., Lab on a Chip, (2007), 7(12):1696-1704.

* cited by examiner

Immunocytochemistry IL-6

Combination Assay Results

Calibration Curve IL-6

Figure 7
Calcium Transient, U2OS Cells
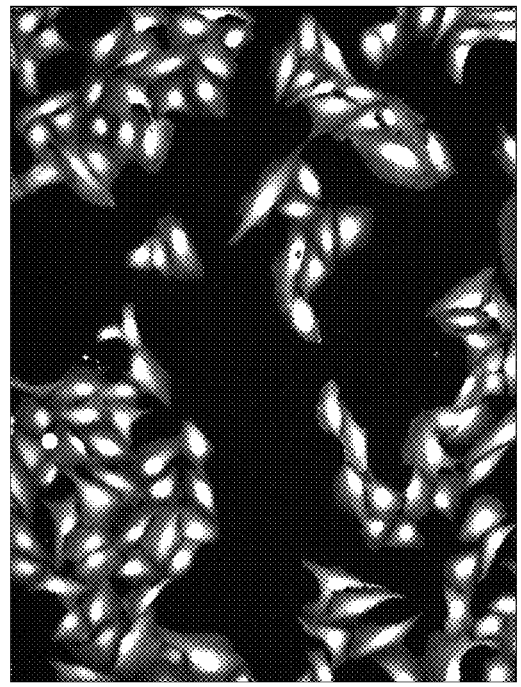
(b) Calcium ionophore stimulated- U2OS cells, showing an increase in intracellular fluorescence
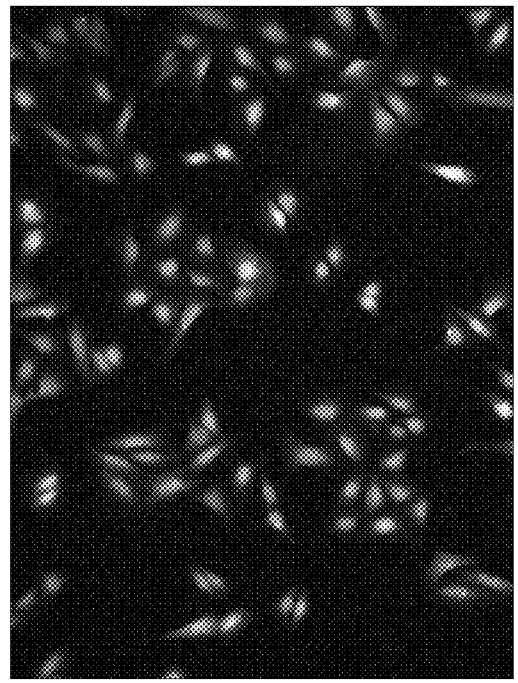
(a) Unstimulated U2OS cells (control)

Relationship between intracellular calcium and cell-associated extracellular IL-6

Ionomycin-stimulated PDGF release from EGFP-NFAT1c transfected U2OS cells

Relationship between NFAT1c translocation and PDGF release from Ionomycin-stimulated U2OS transfected cells Relationship between NFAT1c translocation & TNFα release from ionomycin+ PMA stimulated U2OS transfected cells

MULTIPLEX CELL SIGNALLING ASSAYS

CROSS-REFERENCE TO RELATED APPLICATIONS

This application is a filing under 35 U.S.C. §371 and claims priority to international patent application number PCT/EP2009/050427 filed Jan. 15, 2009, published on Jul. 23, 2009, as WO 2009/090215, which claims priority to patent application number 0800938.3 filed in Great Britain on Jan. 18, 2008.

FIELD OF THE INVENTION

The present invention relates to high-content cellular screening assays, and more particularly to assays for screening for cell stimulation agents and employing multiplex monitoring of reporters in single cells or single populations of cells.

BACKGROUND OF THE INVENTION

The process of discovering a new therapeutic agents, traditionally involves the following stages: i) identification of a drug target, ii) validation of the target, iii) screening for compounds that affect the activity of the target, iv) testing lead compounds for toxicity, v) testing lead compounds for side effects, and vi) examining the metabolism and stability of lead compounds, in the patient or in an appropriate model system. Once a potential therapeutic target has been identified and validated, the initial stage of drug discovery requires the screening of often hundreds of thousands of compounds to identify those that regulate the target in the appropriate therapeutic manner. This screening process requires the development of assay techniques which can quickly and inexpensively measure the potency of compounds that regulate the target factor of interest. These high-throughput screening assays can take various forms that include either cell-based or biochemical assays that often rely on colorimetric, fluorescence, radiometric or luminescence-based detection in order to measure receptor activation, RNA, protein concentration, enzyme activity or the physical interaction of proteins to form a functional complex. A constant challenge facing the drug discovery field is to increase the speed and efficiency by which potential lead compounds are identified from the tens of thousands of chemical compounds tested in compound library screens, and thereafter optimised into new pharmacological agents. A common problem encountered during lead optimisation is that the drug candidate originally identified by virtue of its ability to modulate the activity of one or a few specific target proteins also often has one or more contraindications. Detrimental effects can be caused by the lack of specificity of a compound, thus causing the agent to target a broad range of factors and biological processes in addition to the intended target. Other areas of concern include drug toxicity and metabolism, such that compounds that elicit toxic responses can disrupt normal cellular and tissue function and lead to cell death. Certain compounds have also been demonstrated to regulate their own metabolism, thereby stimulating the breakdown of the target agent and excretion from the body leading to decreased drug efficacy.

Current high throughput screening assays generally focus on measuring the effectiveness of compounds in regulating the activity of a single factor or target, and rely on extended processes of secondary screening and follow-up analyses in order to determine other characteristics of compound function, such as specificity and toxicity. This increases the amount of time and cost required to develop and optimize compounds into drugs with high therapeutic indices (i.e. high efficacy, high specificity, low toxicity). As a result, many compounds, originally selected because of their activity on the target, are eventually discarded because of subsequently discovered side effects, resulting in wasted effort on evaluating drug leads which ultimately prove unsatisfactory.

In the process of drug discovery and lead optimisation, there is a requirement for faster, more effective, less expensive and especially information-rich screening assays that provide simultaneous information on various compound characteristics and their affects on various cellular pathways (i.e. efficacy, specificity, toxicity and drug metabolism).

One approach that has been previously taken, for example, is described in US 2005/0164321 (Promega Corp) which describes a method using enzyme-mediated reactions for multiplex luminogenic and non-luminogenic assays in the same well to detect the amount (e.g., activity) or presence in a sample of one or more moieties, including cofactors for enzymatic reactions such as ATP, proteins (peptides or polypeptides) that bind to and/or alter the conformation of a molecule, e.g., proteins that modify or cleave a peptide or polypeptide substrate, or a molecule which is bound by and/or altered by a protein.

WO 98/58074 (Allelix Biopharma) describes assay methods and compositions useful for screening chemical compounds to identify ligands for receptors including G-protein coupled receptors. The invention employs cells in which a receptor of interest is coupled through a second messenger system to an ion channel that is gated by cyclic nucleotide. Receptor stimulation causes the second messenger system to produce cyclic nucleotide, which results in a measurable ion influx through the channel. The invention also provides a multiplexed system in which mixed cell cultures expressing different receptor types are loaded with different fluorescent reporters of ion influx.

EP1439384 (Cellomics Inc) provides methods and analytical systems for the determination of the distribution, environment, or activity of fluorescently labelled reporter molecules in cells for the purpose of screening large numbers of compounds for those that specifically affect particular biological functions.

Bertelsen, M., (Methods in Enzymology, (2006), 414, 348-363) describes multiplex analysis of inflammatory signalling with intracellular protein translocation using a high-content imaging system.

Howell, B. J. et al. (Methods in Enzymology, (2006), 414, 284-300, 2006) describe the development and implementation of multiplexed cell-based imaging assays for monitoring cell proliferation, cell cycle stage and apoptosis employing fluorescence microscopy.

Nickischer, D. et al. (Methods in Enzymology, (2006), 414, 389-418) describe the development and implementation of three mitogen-activated protein kinase (MAPK) intracellular signalling pathway imaging assays to provide MAPK module selectivity profiling for kinase inhibitors: MK2-EGFP translocation, c-JUN and ERK activation.

Hanson, B. et al. (J. Biomolecular Screening, (2006), 11, 644-651) describe multiplex intracellular assays through the combination of a fluo-4 calcium mobilisation assay and the beta lactamase reporter system, enabling two G-protein coupled receptor assays drug screens with one cell line.

Jonas, J-C. et al. (Diabetes, (1998), 47, 1266-1273) describe the temporal and quantitative relationship between intracellular $Ca^{2+}$ concentration and extracellular insulin secretion from a cellular perfusate of isolated pancreatic islet cells stimulated with glucose. Cultured islets were loaded with the calcium indicator fura-PE3 in a medium containing glucose and one islet transferred to a perfusion chamber. The $[Ca^{2+}]$ was measured by fluorescence microscopy, while insulin was determined by RIA from fractions collected downstream from the perfusate. This publication therefore describes the relationship between $[Ca^{2+}]$ and insulin secretion from a large, mixed (i.e. heterogeneous) population of cells, and thus there is no specific correlation between cell stimulation and associated analyte production at the single cell level. Furthermore, Jonas et al does not describe multiplexed assays or the measurement of cell-associated molecules/analytes.

Marriott et al. (J. Cellular Physiology, 1998, 177, 2, 232-240) describe induction of interleukin-6 mRNA expression and cellular calcium measurements in murine peritoneal macrophages. Both mRNA and cellular calcium measurements are intracellular events as mRNA is not secreted by the cell.

Veronesi et al. (Neurotoxicology, 2003, 24, 463-473) describe intracellular calcium and extracellular IL-6 measurements from broncheal-tracheal epithelial cells. In this paper, IL-6 is not cell associated and is measured downstream by ELISA. The measurement of intracellular calcium and extracellular IL-6 measurements from human monocytes by downstream radioimmunoassay, which are carried out without a cellular washing step, is described by McMillen et al. (Critical Care Medicine, 1995, 23, (1) 34-40).

Drucker et al. (Blood, 2002, 100 (11) Abstract number 5025) report intracellular calcium and extracellular IL-6 measurements from multiple myeloma cell lines by downstream ELISA without a cellular washing step.

The measurement of intracellular calcium and neuropeptide Y (NPY) immunochemical staining in the same population of cells is disclosed by Kohno et al. (Diabetes, 2003, 52, (4) 948-956). NPY was detected following cellular fixation with 4% paraformaldehyde on non-living cells.

Lundgren et al. (World Journal of Surgery, 1996, 20, (7) 727-735) describe intracellular calcium and extracellular PTH measurements from human parathyroid cells by downstream radioimmunoassay, without use of a cellular washing step.

None of the above methods give temporal and multiplexed, high content information from stimulated live cells where intracellular and cell-associated signalling factors are measured in a cell from a single homogeneous population of cells. The above methods are therefore unable to correlate specific intracellular events and the downstream production of cell-associated analytes. The present invention addresses these limitations as well as providing numerous advantages over known methods.

SUMMARY OF THE INVENTION

The present invention provides methods useful in multiplex cell-based assays for compound screening employing imaging instrumentation, which assays offer high content information relating to the biological potency of test agents, off-target effects and cellular toxicity of potential drug candidates. Thus, according to a first aspect of the present invention, there is provided a method for measuring at least one intracellular event and a cell-associated analyte in a single population of living cells wherein the at least one intracellular event and the cell-associated analyte are each components of a concerted biochemical process operating in the cells, the method comprising the steps of:

a) providing a sample containing a single population of living cells;
b) contacting at least one living cell in the single population of cells with a test agent causing or suspected of causing the at least one cell to produce a cell-associated analyte;
c) measuring a change in a physical property in the at least one cell as a measure of at least one intracellular event;
d) washing the cells to remove extracellular fluids;
e) measuring the presence, amount or activity of the cell-associated analyte; and correlating the change in the at least one intracellular event in the at least one cell with the presence, amount or activity of the cell-associated analyte.

The present invention therefore provides an integrated high-content, high-throughput cell-based assay method capable of yielding data on biological activity of exogenous agents acting upon cells. Living cells are constantly responding to essential signals in their environment through a complex network of biochemical pathways regulated in time and space, to provide a cell with an integrated exchange of information that is essential for coordinated responses. Hormones, growth factors and neurotransmitters are among the signalling agents that have been the most extensively studied. Moreover, the present invention provides an information-rich method for measuring multiple events taking place in the same cell, which method is capable of assisting with biochemical pathway analysis. This, in turn, will help to elucidate the various pathways associated with such clinical conditions as cancer, atherosclerosis, psoriasis, rheumatoid arthritis, multiple sclerosis, asthma and chronic obstructive pulmonary disease. Suitably, the sample employed in the method herein described, will contain a single population of cells. According to the method, cells are contacted with a test agent to stimulate the cells to trigger a cascade of downstream biochemical processes (or events). Such processes may result in altered levels of intracellular hormones, second messengers, gases, enzymes, transcription factors, response elements and/or products of gene expression. Furthermore, it is possible to correlate changes in observed intracellular events following cell stimulation, as characterised by a change in the levels or amounts of one or more corresponding intracellular effector molecules, with the formation of cell-associated analytes that may be produced in response to such cell stimulation.

In one embodiment, the changes in the intracellular event and changes in the presence, amount or activity of a cell-associated analyte measured in the presence of a test agent may be compared with control values for each of the at least one intracellular event and the presence, amount or activity of said cell-associated analyte in the absence of the test agent. The control value may be conveniently stored electronically in a database or other electronic format.

The test agent may be a chemical entity such as a drug, a food dye, a hormone, a toxin, an alkylating agent, an oxidising agent, or a carcinogen. Alternatively, the test agent is a physical agent such as electromagnetic radiation (e.g. UV, X-ray, microwave), $\beta^-$ radiation, or heat.

It will be understood by the skilled person that washing step d), to remove extracellular fluids, may be carried out after step b) but before step c).

As disclosed herein, the term "multiplex assay" or "multiplex method" relates to or is a method of measurement or communication of information or signals from two or more messages from the same source (an example of a muliplex assay is described by Ugozzoli, et al. (Analytical Biochemistry, 2002, 307, 47-53).

The term, "high-content screening", as used herein, is a drug discovery method that uses living cells as the test tube for molecular discovery. It describes the use of spatially or temporally resolved methods to discover more from an individual experiment than one single experiment with one output alone. It uses a combination of cell biology, with molecular tools, typically with automated high resolution microscopy and robotic handling (Giuliano et al., J Biomol Screen., 1997, 2, 249-259). The method described herein describes use of an assay method with living cells.

As disclosed herein, the term "intracellular event" is intended to mean a basic cellular process associated with cell signalling and signal transduction, including for example, receptor activation, calcium release, second messenger production, nitric oxide release, phosphorylation, enzyme activation, activation of transcription factors and response elements and gene expression. Thus, in the context of the present invention, detecting a change in a physical property as a measure of the intracellular event is intended to mean the detection of the presence or absence, or the measurement of a change in a level or in the amount of an intracellular effector molecule, or change in the activity of an intracellular enzyme, second messenger, nitric oxide, transcription factor, response element or one or more products of gene expression. Preferably, the intracellular event is an increase in ion concentration (for example intracellular calcium) and/or an increase in gene expression.

As disclosed herein, the term "cellular process" is intended to include the normal processes which living cells undergo and include: biosynthesis, uptake, transport, regulation, receptor binding and internalisation, metabolism, cell physiology, biochemical response, cellular respiration, growth and cell death. Additional cellular processes may include cell adhesion, in which cells become attached to another cell or to an underlying substrate or matrix via cell adhesion molecules, cell signalling, morphogenesis, reproduction and response to stimuli.

As disclosed herein, the term "cell-associated analyte" is intended to refer to a cellular component that is produced upon stimulation of a cell generally by a concerted biochemical process or pathway and which may subsequently be secreted by the cell but which is physically associated with the cell at the time of measuring the presence, amount or activity of the cell-associated analyte. The present invention describes combination or multiplex assays that are designed to measure two or more different analytes present in intracellular and extracellular fluids. For example, intracellular molecules may be present within the cell cytoplasm and nucleus, whereas cell-associated analytes may be present within fluids bathing the immediate surface of the cell. In a preferred embodiment, the assay is designed to measure a cell-associated analyte that is closely associated with the cell, for example bound to the cell membrane, or alternatively present in the immediate environment of the cell, since this gives an accurate measure of the level of expression and temporal nature of the level of generation of the secreted factor or analyte.

The methods of the present invention are applicable in virtually any type of cell. In one embodiment, the population of cells are normal (i.e. un-modified) cells derived from any recognised source with respect to origin including cells of mammalian, bacterial, plant, insect and yeast. In a preferred embodiment, eukaryotic cell types are employed, for example, mammalian cells. Examples include CHO, 3T3, Cos-7, HEK-293, Jurkat, HeLa, Sf-9, HUVEC, HMEC, HL-60, U2OS, J774, BHK, ECV304 and THP-1 cells. Alternative cells include yeast and insect cells.

In another embodiment, cells are modified by transfection with a recombinant expression vector comprising a first reporter gene construct comprising a nucleic acid sequence encoding a first detectable reporter molecule operably linked to and under the control of an expression control element. In this embodiment, suitably, the contacting step b) according to the first aspect is performed under conditions permitting expression of the reporter gene construct.

As disclosed herein, the term "operably linked" indicates that the elements comprising the reporter gene construct are arranged such that they function in concert for their intended purposes, i.e. the reporter gene construct is arranged such that transcription initiates in a promoter and proceeds through the DNA sequence coding for the reporter molecule.

In a further embodiment, the reporter gene construct may additionally encode a protein interest, for example the green fluorescent protein (GFP), a nitroreductase (NTR) reporter or a luciferase gene that catalyzes a reaction with luciferin to produce light.

Another common reporter in bacteria is the lacZ gene which encodes the protein β-galactosidase, thereby causing cells expressing the gene to appear blue when grown on a medium containing the substrate analog X-gal.

As described herein, a reporter gene (or reporter) is a gene that is attached to another gene (expressing, for example a luciferase) of interest in cells in culture. Certain genes are chosen as reporters, either because the characteristics they confer on organisms expressing them can be readily identified and measured, or because the genes are selectable markers of an intracellular event or molecule and can therefore be used in techniques such as GFP translocation assays. Reporter genes are used to determine whether the gene of interest has been taken up by the cells or is expressed, or if gene expression is activated or altered in the cell or cell population. In order to introduce a reporter gene into an organism, the reporter gene and the gene of interest are placed in the same nucleic acid construct which is to be inserted or transfected into the cell or cell population. For example, for bacteria or eukaryotic cells in culture, the construct is usually in the form of circular (plasmid) DNA as is well known.

In one embodiment, cells modified by transfection with a first reporter gene construct comprise a nucleic acid sequence encoding a fluorescent protein, for example a Green Fluorescent Protein (GFP) or a functional GFP analogue derived from Aequorea Victoria. Preferred fluorescent proteins for use in the disclosed method include EGFP (Cormack, B. P. et. al., Gene, (1996), 173, 33-38); EYFP and ECFP (U.S. Pat. No. 6,066,476, Tsien, R. et. al.); F64L-GFP (U.S. Pat. No. 6,172,188, Thastrup, O. et. al.); BFP, (U.S. Pat. No. 6,077, 707, Tsien, R. et. al.). Other fluorescent proteins include NFP (Clontech) and *Renilla* GFP (Stratagene).

In another embodiment, the modified cells comprise a first reporter gene construct comprising a nucleic acid sequence encoding an enzyme, for example a luciferase, a β-galactosidase, an alkaline phosphatase and a nitroreductase. In a particularly preferred embodiment, the reporter gene construct encodes a nitroreductase. Suitable enzyme reporters are those which are capable of generating a detectable (e.g. a fluorescent or a luminescent) signal in a substrate for that enzyme. Particularly suitable enzyme/substrates include: luciferase/ luciferin; β-galactosidase/DDAO galactoside; β-galactosidase/fluorescein di-β-D-galactopyranoside; alkaline phosphatase/Attophos; nitroreductase/CYTOCY5S™ (as disclosed in WO 2005/118839).

Methods for using a variety of enzyme genes as reporter genes are well known (for a review see Naylor L. H., Biochemical Pharmacology, (1999), 58, 749-757). The reporter gene is chosen to allow the product of the gene to be measurable in the presence of other cellular proteins and is introduced into the cell under the control of a chosen regulatory sequence which is responsive to changes in gene expression in the host cell. Typical regulatory sequences include those responsive to hormones and other cellular control and signalling factors. For example, agonist binding to seven transmembrane receptors is known to modulate promoter elements including the cAMP responsive element, NFAT, SRE and AP1; MAP kinase activation leads to modulation of SRE leading to Fos and Jun transcription; DNA damage leads to activation of transcription of DNA repair enzymes and the tumour suppressor gene p53. By selection of an appropriate regulatory sequence, the reporter gene can be used to assay the effect of added agents on cellular processes involving the chosen regulatory sequence under study.

For use as a reporter, a nitroreductase gene may be isolated by well known methods, for example by amplification from a cDNA library by use of the polymerase chain reaction (PCR) (Molecular Cloning, A Laboratory Manual $2^{nd}$ Edition, Cold Spring Harbour Laboratory Press 1989 pp 14.5-14.20). Once isolated, the nitroreductase gene may be inserted into a vector suitable for use with mammalian promoters (Molecular Cloning, A Laboratory Manual $2^{nd}$ Edition, Cold Spring Harbour Laboratory Press 1989 pp 16.56-16.57) in conjunction with and under the control of the gene regulatory sequence under study. The vector containing the nitroreductase reporter and associated regulatory sequences may then be introduced into the host cell by transfection using well known techniques, for example by use of DEAE-Dextran or Calcium Phosphate (Molecular Cloning, A Laboratory Manual $2^{nd}$ Edition, Cold Spring Harbour Laboratory Press 1989 pp 16.30-16.46). Other suitable techniques will be well known to those skilled in the art. Nitroreductase has been shown to be retained in cells when expressed in this manner (see Bridgewater et al, Eur. J. Cancer, (1995), 31a, 2362-70).

A DNA construct may be prepared by the standard recombinant molecular biology techniques of restriction digestion, ligation, transformation and plasmid purification by methods familiar to those skilled in the art and are as described in Sambrook, J. et al (1989), Molecular Cloning—A Laboratory Manual, Cold Spring Harbor Laboratory Press. Alternatively, the construct can be prepared synthetically by established methods, e.g. the phosphoramidite method described by Beaucage and Caruthers, (Tetrahedron Letters, (1981), 22, 1859-1869) or the method described by Matthes et al (EMBO J., (1984), 3, 801-805). According to the phosphoramidite method, oligonucleotides are synthesised, e.g. in an automatic DNA synthesizer, purified, annealed, ligated and cloned into suitable vectors. The DNA construct may also be prepared by polymerase chain reaction (PCR) using specific primers, for instance, as described in U.S. Pat. No. 4,683,202 or by Saiki et al, (Science, (1988), 239, 487-491). A review of PCR methods may be found in PCR protocols, (1990), Academic Press, San Diego, Calif., U.S.A.

During the preparation of the DNA construct, the gene sequence encoding the reporter must be joined in frame with the cell cycle phase specific destruction control element and optionally the spatial localisation control element. The resultant DNA construct should then be placed under the control of a suitable cell cycle phase specific expression control element.

Measurement of an intracellular event, for example changes upon cell stimulation in the levels of a hormone, a second messenger, or calcium may be suitably accomplished by detecting and quantitating fluorescence emitted by the cell by employing a fluorescent probe specific for such a molecule. The measurement of intracellular hormones, second messengers, transcription factors and the like may be accomplished by known methods. Examples of intracellular events and the associated effector molecules that may be measured include:

i) Cellular Calcium Flux or Calcium Transient Assays

Such assays employ a cell permeable fluorescent indicator dye molecule such as Fluo-2 and Fluo-4, such that there is an increase in fluorescence emission as a result of the binding of the probe to the calcium ions. See for example, "Cellular Calcium, A Practical Approach", Edited by McCormack and Cobbold (1991), IRL Press.

ii) GFP-Tagged Translocation Assays

These assays require a nucleic acid construct expressing GFP so that protein translocations occurring between the cytoplasm and either the cell membrane, early endosomes or the nucleus can be identified. See for example, Hancock et al, The Society for Biomolecular Screening, $9^{th}$ Annual Conference and Exhibition, Drug Discovery at the Cutting Edge, (2003), Portland, Oreg. which describes live intracellular GFP-tagged protein translocation assays for the monitoring and quantitation of a variety of signalling events including activation of AKT-1.

iii) Reporter Gene Assays

Reporter gene assays may be used to assay for the expression of a gene of interest, producing a cellular protein that has little obvious or immediate effect on the cultured cells. Here, the reporter is directly tagged to the gene of interest to create a gene fusion. The two genes are under the control of the same promoter and are transcribed into a single messenger RNA molecule, which is translated into protein, e.g. an enzyme reporter. It is important in these examples that both proteins are able to properly fold into their active conformations and interact with their enzyme substrates despite being fused. In forming the DNA construct, a segment of DNA coding for a flexible polypeptide linker region is often included such that interference between the reporter and the gene product is minimised. Examples of such approaches are well known, see for example, Bronstein et al, Chemiluminescent and Bioluminescent Reporter Gene Assays, Analytical Biochemistry, (1994), 219, 169-181.

iv) Cellular Lysis Assays

Here, intracellular components are measured in a cell lysis fluid, often coupled with detergents which are used to dissociate the cell membrane. Examples of such cell lysis steps and assays may be found in U.S. Pat. No. 6,900,019 (Horton). Assays to measure the presence, amount or activity of a cell-associated analyte are well known, and include immunocytochemistry, protein-binding assays and enzyme assays. Components of an assay may typically comprise:

a) a sample of cells containing or suspected of containing the analyte to be measured;
b) an unlabelled specific binding partner of the analyte which is, or is capable of being, immobilised onto a solid support;
c) a specific binding partner, or an analogue, of the analyte, which is either labelled or unlabelled and capable of being labelled.

In one embodiment, the assay is an enzyme-assay. In this format, components a), b) and c) are contained in the wells of a microwell plate, component c) being an enzyme-labelled specific binding partner of the compound being tested for. The assay measurement is initiated by the addition to the wells of detection reagents suitable for the detection of the enzyme label. See for example, Berg, J., Tymoczko J and Stryer L, Biochemistry, W.H. Freeman and Company, (2002).

In another embodiment, the labelled specific binding partner can include a fluorescence label. Suitable fluorescent labels for use in the measurement of analytes by immunocytochemistry assay method will be well known and will include for example, fluorescein, rhodamine and cyanine dyes.

In another embodiment, an enzyme-linked immunospot (ELISPOT) assay is employed for measurement of the cell-associated analyte. See Czerkinsky, C., et al, J. Immunol. Methods, (1983), 65 (1-2), 109-21). In this embodiment, cell-associated analytes may be measured with a translucent (PVDF) membrane acting as a solid-support for antibodies or other binding reagents, and detecting the cell-associated analyte with an enzyme-labelled probe and fluorescent substrate.

In a still further embodiment, the measurement of cell-associated analyte can be performed using the live cell-ELISA technique, in which a sample of cells possibly containing the analyte to be measured is contained in a vessel, and the cell-associated analyte is detected with suitable probes and luminescent or fluorescent substrates. See for example, Grunow, R. et al, J. Immunological Methods, (1994), 171, 93-102.

The nature of the cell-associated analyte is not material to the invention, except insofar as the presence, activity or amount of the analyte can be correlated with an intracellular event (as measured by a change in an intracellular component, or reporter gene activation, or GFP translocation). Any cell-associated analyte for which a specific binding partner is available can in principle be utilised in the invention. Typical specific-binding partner combinations suitable for use with the invention may be selected from: hapten-antibody, ligand-receptor, DNA-DNA, RNA-RNA, DNA-RNA, biotin-streptavidin, protein-antibody, peptide-antibody, and polypeptide-antibody interactions. Preferably, a specific binding assay is a protein-binding assay or more particularly an immunocytochemistry assay. Typical analytes include proteins, peptides, neurotransmitters, neurotrophins, vitamins, peptide hormones, enzymes, growth factors, steroids, prostaglandins, integrins, matrix components, adhesins, cluster of differentiation molecules, cytokines, chemokines, lymphokines and leukotrienes and the like.

Measurement of certain intracellular components are indicative of a change in an intracellular event and such components include second messengers, ADP, ATP, AMP, cyclic ADP-ribose, cellular calcium, cGMP, cAMP, $IP_3$, $IP_1$, $IP_4$, serine-threonine kinases, PI3-kinase, diacylglycerol, AKT-1, ribosomal protein S6 kinase, SMAD-9, phospholipase C, phospholipase C delta-1, amyloid beta precursor protein, ras homolog gene family, member A.PARAPARA (ARHA), receptor-interacting serine/threonine kinase 2, heat-shock 70-kD protein 1A, (HSPA1A), sphingosine kinase-1 (SPHK1), SPHK2, Forkhead Box O1A (FOXO-1A), glucocorticoid receptor (GCCR), caspases, AKT1 and transcriptional factors. Individually, these intracellular analytes may be measured, for example, using GFP translocation markers, reporter-gene assays, fluorescent or luminescent probes, enzyme-mediated assays, protein-binding techniques, electrophysiology, spectroscopy, nuclear magnetic resonance techniques, flow cytometry, ion transport, microscopy and radiometric assays.

The detection and measurement of changes in fluorescence intensity may be made using an optical imaging method employing instruments incorporating a charge coupled device (CCD) imager (such as a scanning imager or an area imager). For example, the LEADSEEKER™ Multimodality Imaging System (GE Healthcare) features a CCD camera allowing quantitative fluorescence imaging of high density microwell plates in a single pass. Alternatively, cells may be imaged in "live cell" format using an IN Cell Analyzer 1000 Optical Imaging System (GE Healthcare). In this format, a suitable cell marker should be introduced into the cell, such as a cytosolic, nuclear or membrane fluorescent label having a fluorescence emission wavelength that is different and distinguishable from the fluorescence emission of the compound of interest.

According to the present invention, methodologies are combined which enable intracellular and extracellular, cell-associated events to be monitored in parallel in single cells or single homogeneous populations of cells treated with test agents. The present invention therefore provides an advantageous method for directly determining the effect of a putative drug, or agent on a single cell or single population of cells, thus reducing the amount of time and cost required to develop and optimize a compound with a high therapeutic effect.

BRIEF DESCRIPTION OF THE DRAWINGS

FIG. 7 shows a calcium transient from calcium ionophore A23187-stimulated human U2OS cells grown in culture obtained in combination data for IL-6 measurement according to Example 4. Image analysis was performed on an IN Cell 1000 Analyzer and imaged using a 10× objective, 505 light pass dichroic 475/535 filter set 200 ms exposure. Fluorescence measurement shows an increase in intracellular calcium (FIG. 7b) compared with the unstimulated (zero ionophore) control (FIG. 7a).

DETAILED DESCRIPTION OF THE INVENTION

Examples

Below the present invention will be disclosed by way of examples, which are intended solely for illustrative purposes and should not be construed as limiting the present invention as defined in the appended claims. All references mentioned below or elsewhere in the present application are hereby included by reference.

Figure 1:
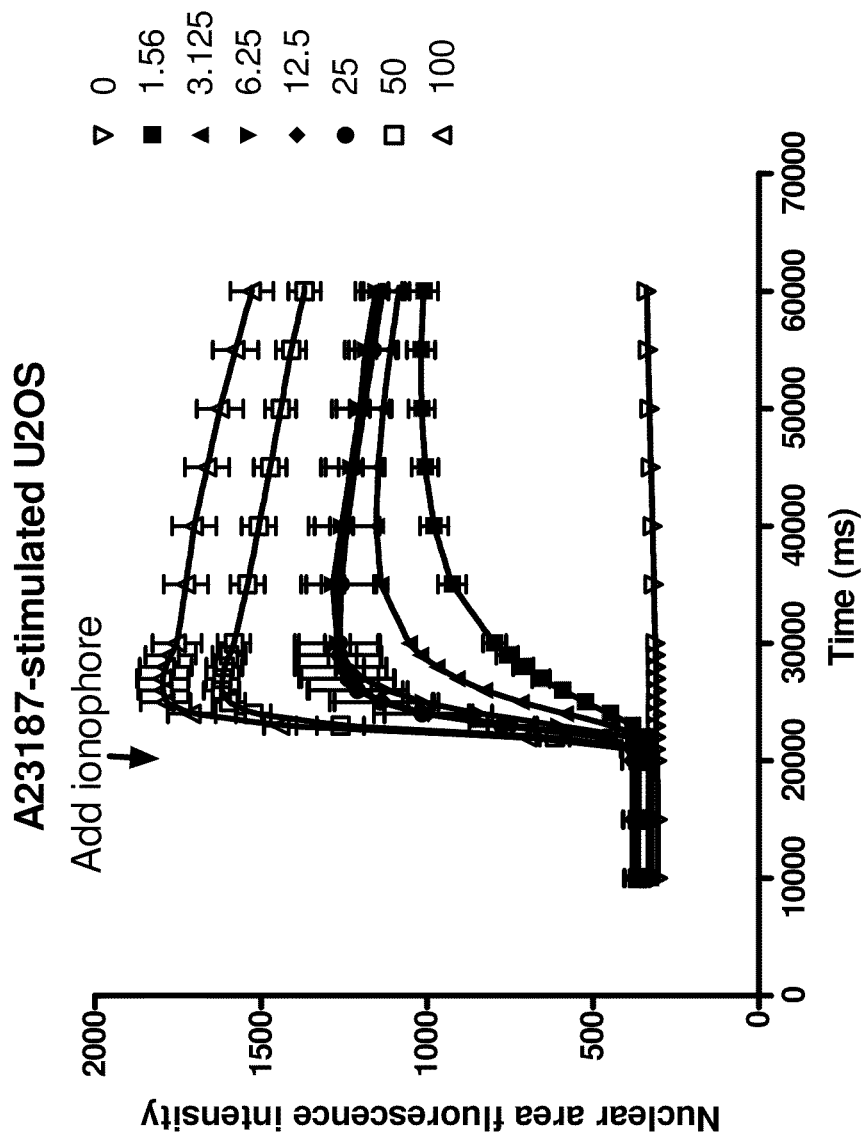
FIG. 1 shows results from a combination assay according to Example 1. An increase in cytosolic intracellular calcium resulting from calcium ionophore A23187-stimulated U2OS cells derived from a single population, was detected by binding to a calcium sensitive, cell permeable dye Fluo-4. Fluorescence emission ($\lambda_{em}$=535 nm) was measured using an IN Cell Analyzer 1000 Optical Imaging System and imaged using a 10× objective, 505 light pass dichroic 475/535 filter set with 200 ms exposure.
Figure 3:
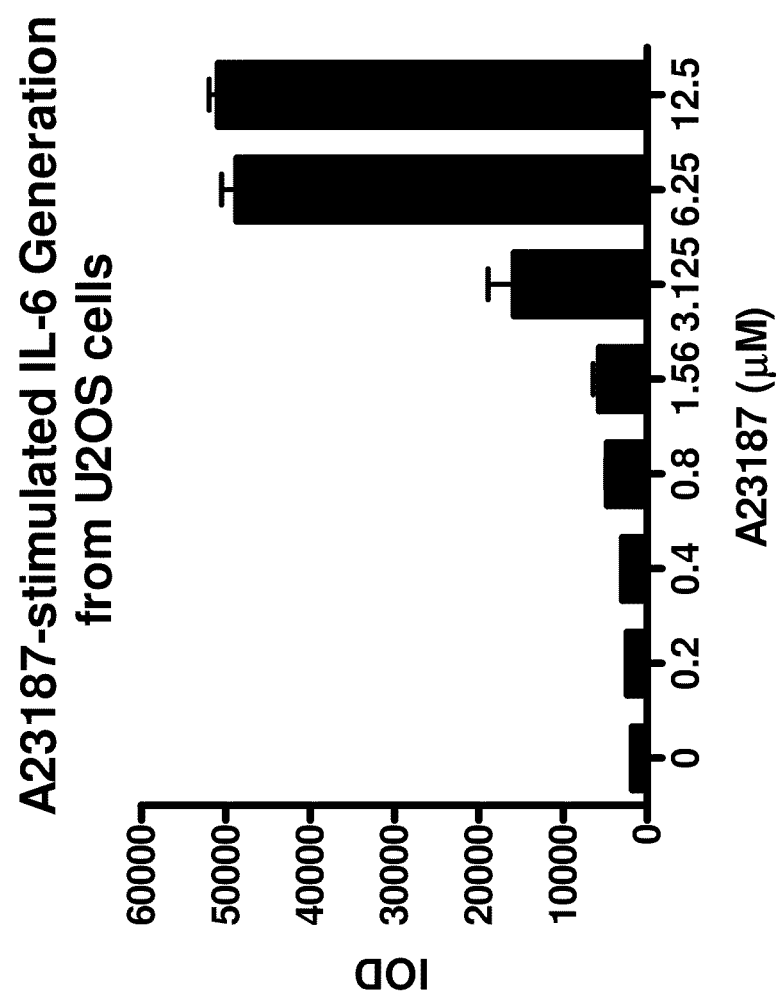
FIG. 3 shows calcium ionophore-stimulated IL-6 generation from U2OS cells demonstrating cell-associated IL-6 secretion from a single population of A23187-stimulated U2OS cells in culture according to Example 3. Cells were contacted with the test agent (calcium ionophore A23187) for 4 hours and cell-associated IL-6 measured post cell-stimulation with the test agent. After stimulation, the cell supernatant was decanted, the cells were washed thoroughly X3 with PBS, before incubating with the anti-IL-6 antibody. The cells were washed ×3 with PBS before addition of the chemiluminescent substrate. Results from the calcium transient were obtained prior to the IL-6 results using the same population of cells. Data was obtained in combination with results shown in FIG. 1. The results (FIG. 3) were obtained using a LEAD-SEEKER™ Multimodality Imaging System, exposing for 20 seconds, using the chemiluminescent substrate and the luminescent signal reporter (anti-IL-6 labelled with the enzyme horseradish peroxidise).

1. Measurement of a Calcium Transient in Ionophore A23187-Stimulated U2OS Cells
Materials
Calcium flux buffer (5 mM KCl, containing 1 mM MgSO4, 100 mM HEPES, 10 mM D-glucose, 145 mM NaCl and 1 mM $CaCl_2$ pH 7.4).
Fluo-4 (InVitrogen)
Hoescht 33342 (InVitrogen)
7.5% albumin (Sigma)
Calcium ionophore A23187 (Sigma)
U2OS cells (European Collection of Cell Cultures, Porton Down, UK)
1.2 Method and Results
i) U2OS cells were seeded into 96-well Greiner cluster plates at 6000 cell/well in 100 µl of complete McKoys media and incubated overnight at 37° C., 5% $CO_2$.
ii) Loading buffer was prepared with 42.8 ml of calcium flux buffer with 6.65 ml of 7.5% albumin This buffer was stored at 37° C.
iii) 120 ml of maintenance buffer was prepared with 118.16 ml calcium flux buffer and 1840 µl of 7.5% albumin
iv) 5 mg of calcium ionophore A23187 was dissolved in 1 ml of DMSO. The ionophore was subsequently diluted in complete maintenance buffer to give final concentration of ionophore over the range of 1.56-100 µM. Fluo-4 dye was prepared by adding 456 µl DMSO to a 50 µg vial, and the vial was mixed well to provide a Fluo-4 stock concentration of 100 µM. 100 µl of 100 µM Fluo-4 dye and 6 µl of 16 mM Hoescht nuclear dye were added to 9.894 ml of loading buffer. The media was removed from the cell culture plate, and 100 µl/well of warmed complete loading buffer was added. The plate was incubated for 40 minutes at 37° C., 5% $CO_2$. Following incubation, the loading buffer was removed and 150 µl/well of maintenance buffer was added. The plate was transferred to an IN Cell Analyzer 1000 (Kinetic Module) using a 10× objective, 505 light pass dichroic 475/535 filter set (Fluo-4), 200 ms exposure, 360/460 filter set (Hoescht), 300 ms exposure. Images were acquired every five seconds after the following time: 0, 5-60 seconds. After 20 seconds the ionophore was dispensed and image acquisition was continued. The results were analysed using an object intensity algorithm (IN Cell Investigator software).
v) FIG. 1 shows the results from a combination assay of intracellular calcium concentration following stimulation by calcium ionophore A23187 (1.56-100 µM) of U2OS cells grown in culture. An increase in cell-associated IL-6, is shown in FIG. 3. The data shows that upon stimulation with the calcium ionophore, the cells respond with an increase in cytosolic intracellular calcium as shown by an increase in emitted fluorescence from the cell permeable dye Fluo-4 ($\lambda_{em}$=535 nm). FIG. 1 shows a rise in intracellular calcium over eight minutes and indicates a temporal change in intracellular calcium levels with a peak and decline. The change in the intracellular event is also dependent on the dose of the calcium ionophore employed in the assay.

2. Measurement of a Calcium Transient in Histamine-Stimulated U2OS Cells
2.1 Materials
Calcium flux buffer (5 mM KCl, containing 1 mM MgSO4, 100 mM HEPES, 10 mM D-glucose, 145 mM NaCl and 1 mM $CaCl_2$ pH 7.4).
Fluo-4 calcium fluor (InVitrogen)
Hoesch 33342 DNA stain (InVitrogen)
7.5% albumin (Sigma)
Histamine (Sigma)
U2OS cells (European Collection of Cell Cultures, Porton Down, UK)

Figure 4:
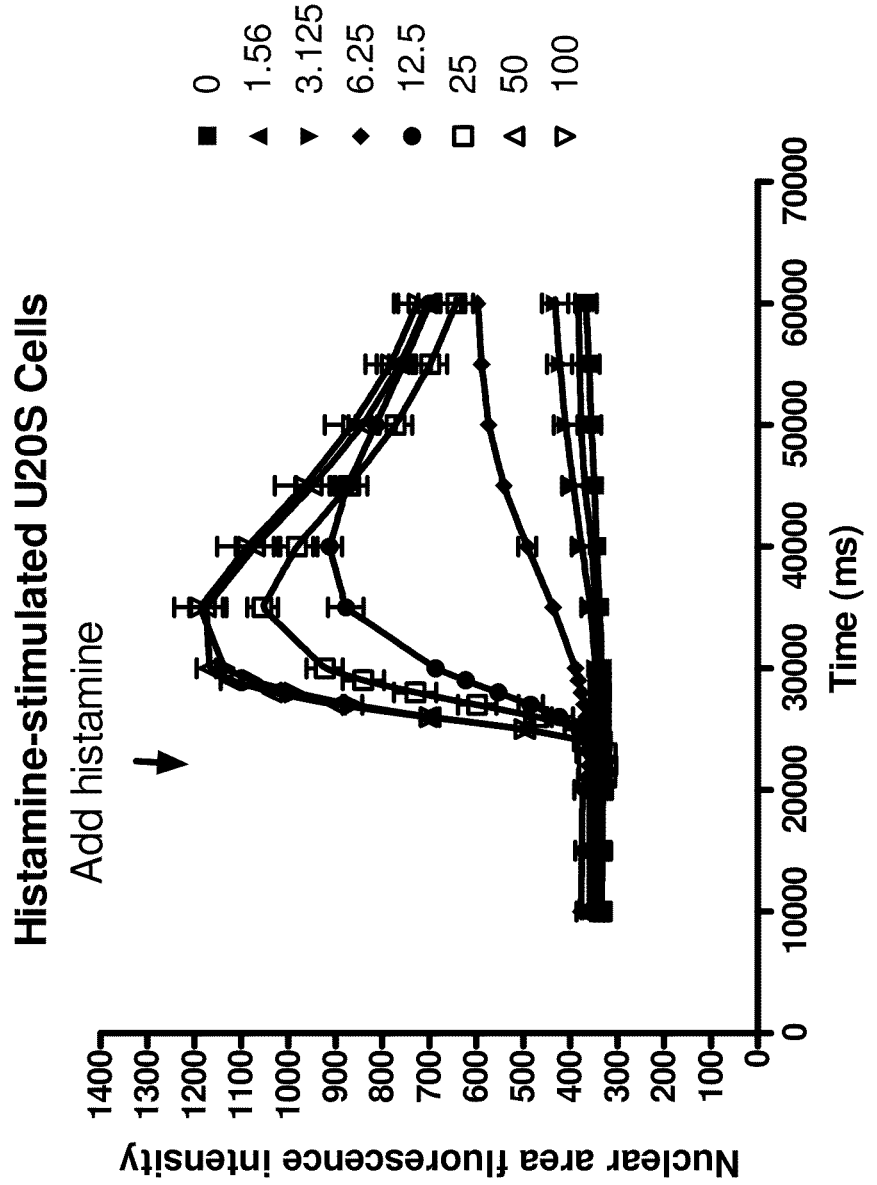
FIG. 4 shows results from a combination assay according to Example 2. An increase in cytosolic intracellular calcium resulting from histamine-stimulated U2OS cells derived from a single population, was detected by binding to a calcium sensitive, cell permeable dye Fluo-4. Fluorescence emission ($\lambda_{em}$=535 nm) was measured using an IN Cell Analyzer 1000 and imaged using a 10× objective, 505 light pass dichroic 475/535 filter set with 200 ms exposure.
Figure 5:
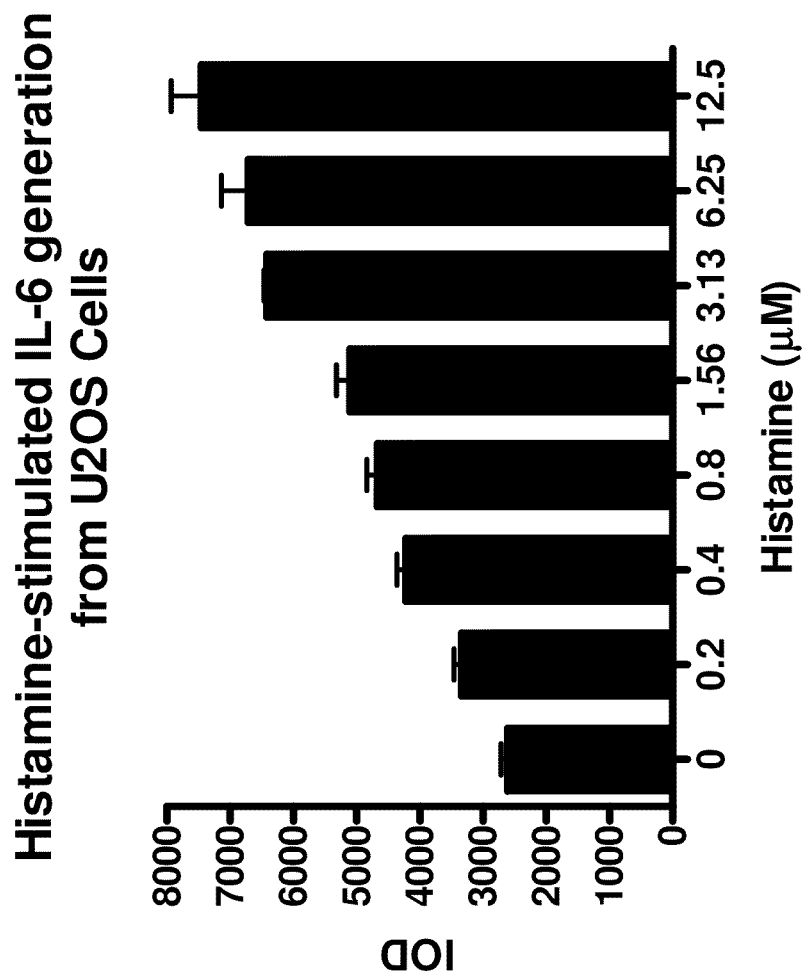
FIG. 5 shows histamine-stimulated IL-6 generation from human U2OS cells derived from a single population, according to Example 3. Cells were contacted with the histamine test agent overnight and cell-associated IL-6 measured post cell-stimulation. The results were obtained on the LEAD-SEEKER™ Multimodality Imaging System, exposing for 20 seconds, using the chemiluminescent substrate and the luminescent signal reporter (anti-IL-6 labelled with the enzyme horseradish peroxidise).

2.2 Method and Results i) U2OS cells were seeded into 96-well Greiner cluster plates at 6000 cell/well in 100 µl of complete McKoys media and incubated overnight at 37° C., 5% $CO_2$.

ii) Loading buffer was prepared with 42.8 ml of calcium flux buffer with 6.65 ml of 7.5% albumin This buffer was stored at 37° C.

iii) 120 ml of maintenance buffer was prepared with 118.16 ml calcium flux buffer and 1840 µl of 7.5% albumin iv) 25.3 mg of histamine was weighed out and dissolved in 1 ml of warmed maintenance buffer. Histamine was subsequently diluted in complete maintenance buffer to give final concentration of histamine over the range of 1.56-100 µM. Fluo-4 dye was prepared by adding 456 µl DMSO to a 50 µg vial, and the vial was mixed well to provide a Fluo-4 stock concentration of 100 µM. 100 µl of 100 µM Fluo-4 dye and 6 µl of 16 mM Hoescht nuclear dye were added to 9.894 ml of loading buffer. The media was removed from the cell culture plate, and 100 µl/well of warmed complete loading buffer was added. The plate was incubated for 40 minutes at 37° C., 5% $CO_2$. Following incubation, the loading buffer was removed and 150 µl/well of maintenance buffer was added. The plate was transferred to an IN Cell Analyzer 1000 (Kinetic Module) using a 10× objective, 505 light pass dichroic 475/535 filter set (Fluo-4) 200 ms exposure, 360/460 filter set (Hoescht), 300 ms exposure. Images were acquired every five seconds after the following times: 0, 5-60 seconds. After 20 seconds the histamine was dispensed and image acquisition was continued. The results were analysed using an object intensity algorithm (IN Cell Investigator software).

v) FIG. 4 shows the results from a combination assay of intracellular calcium concentration following histamine stimulation (1.56-100 µM) of U2OS cells grown in culture. An increase in cell-associated IL-6, is shown in FIG. 5. The data shows that upon stimulation with the histamine test agent, the population of cells respond with an increase in cytosolic intracellular calcium as shown by an increase in emitted fluorescence from the cell permeable dye Fluo-4 ($\lambda_{em}$=535 nm). FIG. 4 shows a rise in intracellular calcium over eight minutes and also indicates a temporal change in intracellular calcium levels with a peak and decline. The change intracellular event is also dependent on the dose of the histamine test agent employed in the assay.

3. Combination Assay of Human Interleukin-6 from Histamine or Calcium Ionophore A23187-Stimulated U2OS Cells Following Measurement of the Calcium Transient 3.1 Materials Anti-human IL-6 antibodies (R&D Systems Q6000B)
Luminescent substrate (R&D Systems Q6000B)
Calcium ionophore A23187 (Sigma)
Histamine (Sigma)
U2OS cells (European Collection of Cell Cultures, Porton Down, UK)

Figure 6:
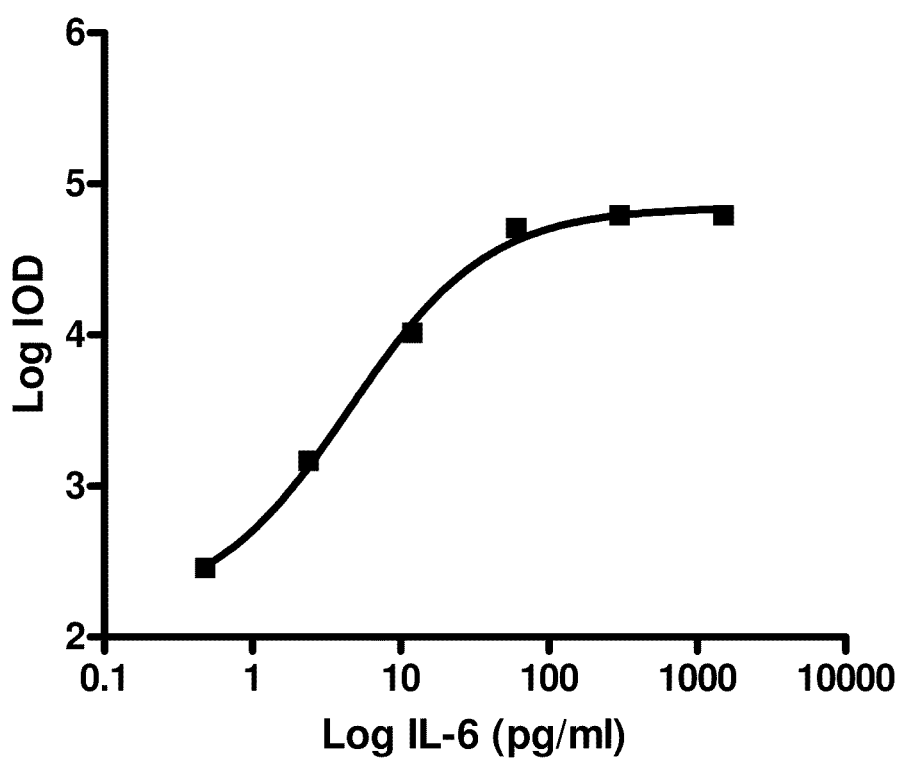
FIG. 6 shows a calibration curve of known amounts of recombinant IL-6, using known amounts of recombinant IL-6 (0.48-1500 pg/ml) using a chemiluminescent assay (R&D Systems, catalogue code Q6000B) according to Example 3. Results were measured on a LEADSEEKER™ Multimodality Imaging System.

3.2 Method and Results i) U2OS cells were seeded into 96-well tissue culture plates at 6000 cell/well in 100 µl of complete McKoys media and incubated overnight at 37° C., 5% $CO_2$.

ii) Cells were stimulated with A23187 or histamine (see Examples 1 and 2 above) and a calcium transient was measured (see FIGS. 1 and 4). After stimulation with ionophore or histamine, the cell supernatant was decanted, the cells were washed thoroughly X3 with PBS, before incubating with the anti-IL-6 antibody. The cells were washed ×3 with PBS before addition of the chemiluminescent substrate. Results from the calcium transient were obtained prior to the IL-6 results using the same single population of cells.

iii) IL-6 data was obtained in combination with results shown in FIGS. 1 and 4. The results (Table 1 and FIG. 3, ionophore stimulation; FIG. 5 histamine stimulation) were obtained on the LEADSEEKER™ Multimodality Imaging System, exposing for 20 seconds, using the chemiluminescent substrate and the luminescent signal reporter (anti-IL-6 labelled with the enzyme, horseradish peroxidase).

iv) The results of the calibration curve using known amounts of recombinant IL-6 as a standard are shown in Table 2 and FIG. 6, allowing accurate measurement of cell-associated IL-6. The results (Table 2 and FIG. 6) show an increase in chemiluminescent signal with increasing concentration of IL-6. These data were obtained on the LEADSEEKER™ Multimodality Imaging System.

TABLE 1

Interleukin-6 sample measurements from stimulated U2OS in culture

| Cell sample number for IL6 measurement | IOD | |
| --- | --- | --- |
| 1 | 1151.51 | 1411.74 |
| 2 | 1698.92 | 1803.51 |
| 3 | 2370.45 | 2417.2 |
| 4 | 3006.14 | 2869.03 |
| 5 | 4554.7 | 4876.76 |
| 6 | 6204.84 | 5156.72 |
| 7 | 17974.71 | 13584.73 |
| 8 | 50076.31 | 51643.99 |
| 9 | 49946.58 | 47382.19 |
| 10 | 37931.93 | 36675.02 |
| 11 | 14217.31 | 16212.06 |
| 12 | 3176.96 | 3308.5 |
| 13 | 2687.38 | 2537.77 |
| 14 | 3193.71 | 3092.18 |
| 15 | 4323.73 | 4128.06 |
| 16 | 3429.57 | 3257.39 |
| 17 | 4793.5 | 4566.47 |
| 18 | 4962.54 | 5262.34 |
| 19 | 6455.98 | 6390.91 |
| 20 | 7017.89 | 6417.23 |
| 21 | 7796.78 | 7123.62 |
| 22 | 7454.8 | 7246.66 |
| 23 | 6511.13 | 6664.44 |
| 24 | 5146.23 | 5008.23 |

TABLE 2

Interleukin-6 calibration curve from an Imaging System

| IL-6 pg/ml | IOD | |
| --- | --- | --- |
| 0.48 | 273.47 | 300.3 |
| 2.4 | 1392.55 | 1530.24 |
| 12 | 9826.55 | 10791.35 |
| 60 | 50222.06 | 51335.14 |
| 300 | 62251.67 | 61541.55 |
| 1500 | 62551.34 | 61015.07 |

4. Combination Assay of Intracellular Calcium and Human Interleukin-6 from Calcium Ionophore A23187-Stimulated U2OS Cells on IN Cell Analyzer 1000

4.1 Materials

Anti-IL-6 (R&D Systems)
Goat anti-human IgG CY™ 5 linked (GE Healthcare)
Calcium ionophore A23187 (Sigma)
U2OS cells (European Collection of Cell Cultures, Porton Down, UK)

Figure 2:
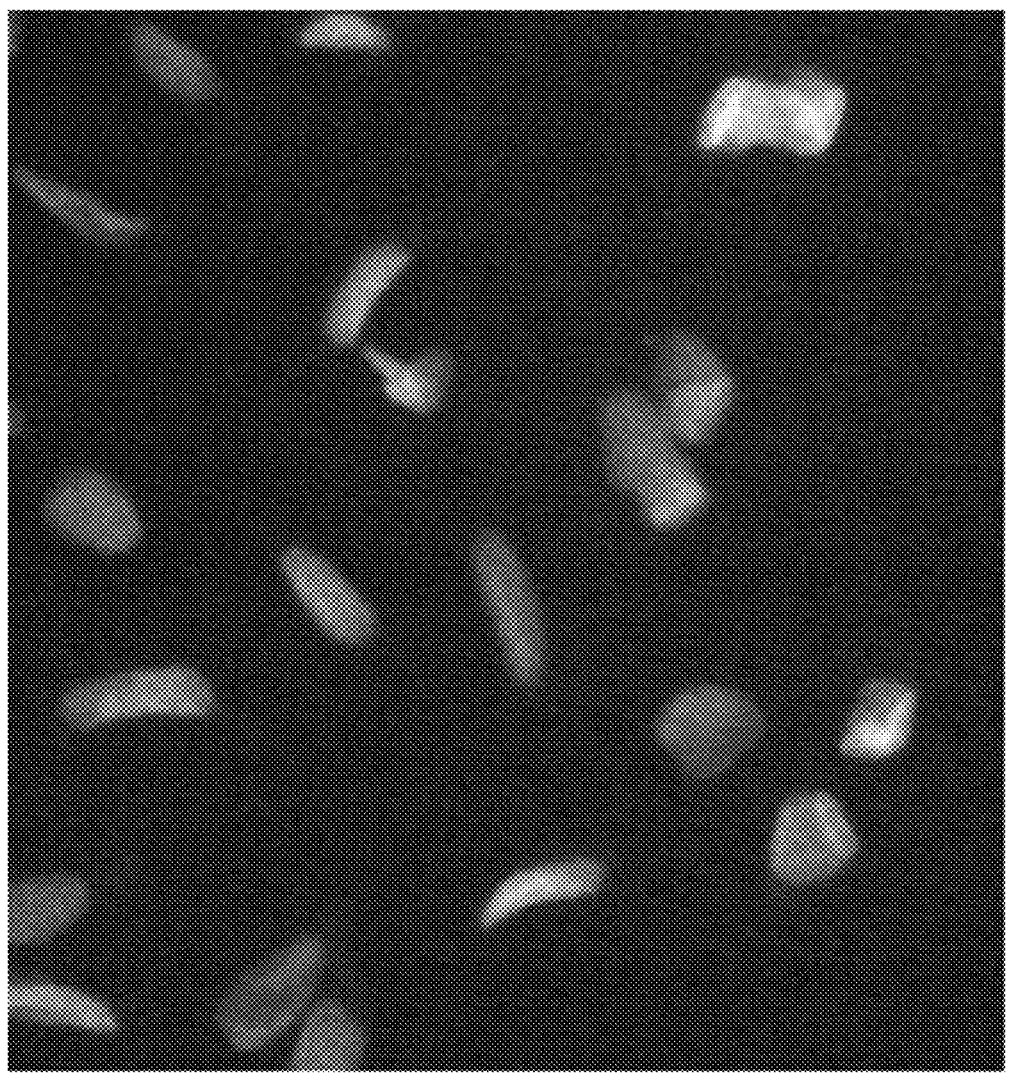
FIG. 2 is an image of an immunocytochemical analysis showing cell-associated, secreted human IL-6 from A23187-stimulated U2OS cells derived from a single population according to Example 4. Fluorescence was measured on an IN Cell Analyzer 1000.
Figure 8:
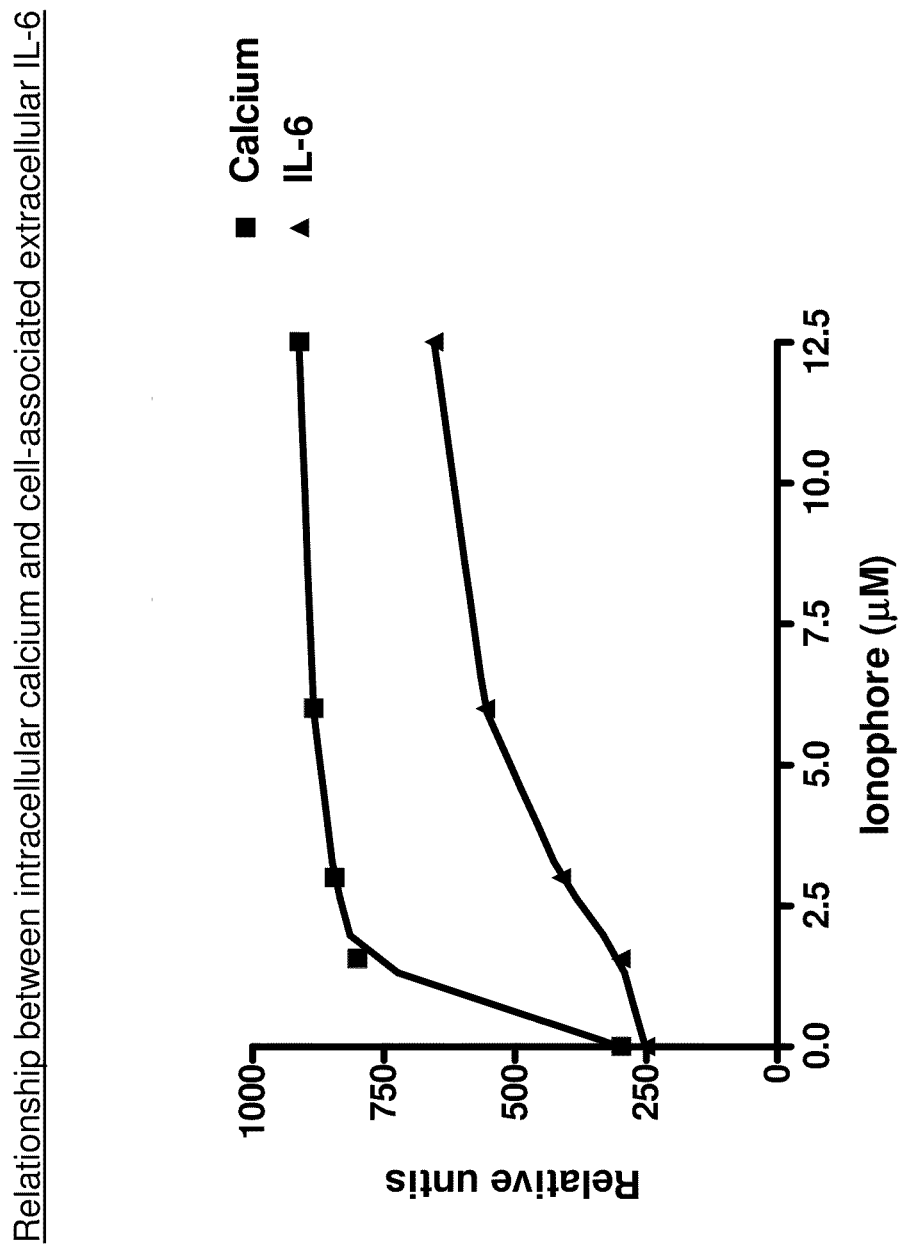
FIG. 8 shows the relationship between intracellular calcium and cell-associated IL-6 from A23187-stimulated U2OS cells, both intracellular and cell-associated molecules exhibiting a dose-dependent rise with increasing concentration of the ionophore A23187. Cells were derived from a single population. Results were obtained using an IN Cell Analyzer 1000 according to Example 4.
Figure 9:
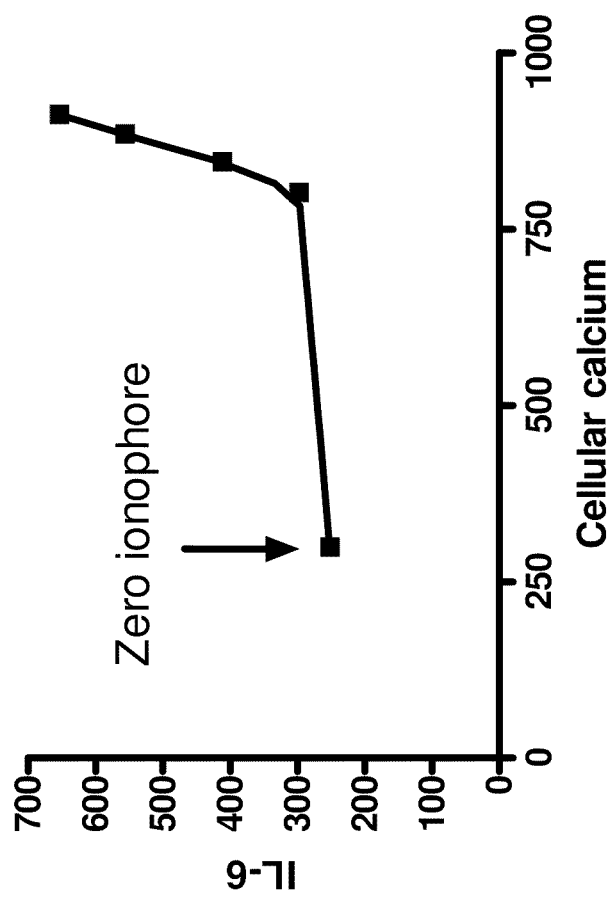
FIG. 9 shows the relationship between intracellular and cell-associated IL-6 from A23187-stimulated U2OS cells derived from a single population. The data shows an increase in intracellular calcium and cell-associated IL-6 when cells are in contact with the test agent only. No correlation between intracellular and cell-associated IL-6 was exhibited with unstimulated (control) cells. Results were obtained using an IN Cell Analyzer 1000 according to Example 4.
Figure 10:
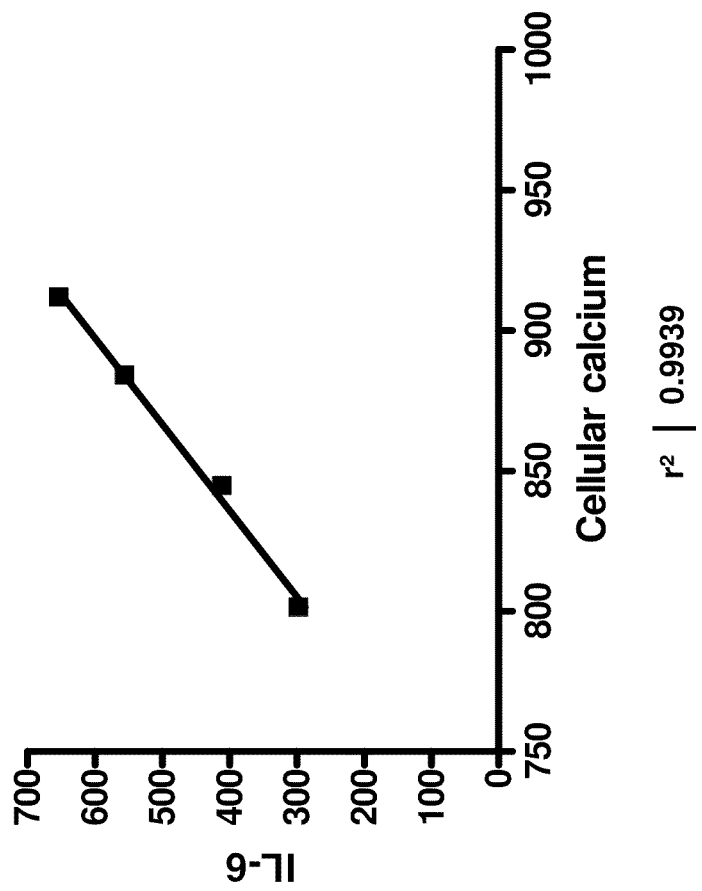
FIG. 10 shows an excellent correlation between intracellular calcium and cell-associated IL-6 from A23187-stimulated human U2OS cells derived from a single population (correlation coefficient >0.99). Results were obtained using an IN Cell Analyzer 1000 according to Example 4.

4.2 Method and Results i) U2OS cells were seeded into 96-well tissue culture plates at 6000 cell/well in 100 µl of complete McKoys media and incubated overnight at 37° C., 5% $CO_2$.

ii) Cells were stimulated with A23187 for 8 minutes before measurement of a calcium transient on an IN Cell Analyzer 1000 as described in Example 1. FIG. 7 shows a calcium transient from calcium ionophore A23187-stimulated human U2OS cells grown in culture obtained in combination data for IL-6 measurement, data which is shown in FIG. 2. The results from this assay were measured on an IN Cell Analyzer 1000 using a 10× objective, 505 light pass dichroic 475/535 filter set 200 ms exposure. Fluorescence measurement shows an increase in intracellular calcium (1.56 µM ionophore) compared with the unstimulated (zero ionophore) control.

iii) FIG. 2 shows immunocytochemistry from a combination assay (with intracellular calcium, see FIG. 1) showing cell-associated IL-6 (the cell-associated analyte) from a population of A23187-stimulated U2OS cells in culture. Cells were contacted with the test agent (calcium ionophore A23187) for 4 hours and cell-associated IL-6 measured post cell-stimulation with test agent. After stimulation with the ionophore, the supernatant was decanted and the cells were washed thoroughly X3 with PBS. Cell-associated IL-6 was localised with an anti-human IL-6 antibody (anti-IL-6 monoclonal antibody) and a fluorescent dye-labelled anti-human IgG (anti-human gG, CY™ 5 linked, (GE Healthcare). After 60 minutes incubation with the monoclonal anti-IL-6 antibody, the cells were washed ×3 and the dye labelled anti-human IgG added. After 60 minutes incubation with the fluor-labelled second antibody, the cell were washed ×3 with PBS, and fluorescence detected on an IN Cell Analyzer 1000, using a 10× objective, 51008bs dichroic 620/700 filter set (CY™ 5 filter set), 500 ms exposure. The results were analysed using an object intensity algorithm (IN Cell Investigator software). The results, (FIG. 2), clearly demonstrate cell-associated IL-6.

iv) FIG. 8 shows the relationship between intracellular calcium and cell-associated IL-6 from A23187-stimulated U2OS cells, both intracellular and cell-associated molecules exhibiting a dose-dependent rise with increasing concentration of the ionophore A23187. Cells were derived from a single population. Results were obtained in an IN Cell Analyzer 1000 Optical Imaging System as described above. The results were analysed using an object intensity algorithm (IN Cell Investigator software).

v) FIG. 9 shows the relationship between intracellular and cell-associated IL-6 from A23187-stimulated U2OS cells derived from a single population. The data shows a biphasic increase in intracellular calcium and cell-associated IL-6 when cells are in contact with the test agent only. No correlation between intracellular and cell-associated IL-6 was exhibited with unstimulated (control) cells. Results were obtained in the IN Cell Analyzer 1000 Optical Imaging System as described above. The results were analysed using an object intensity algorithm (IN Cell Investigator software).

vi) FIG. 10 shows a correlation between intracellular calcium and cell-associated IL-6 from A23187-stimulated human U2OS cells derived from a single population (correlation coefficient>0.99). Results were obtained in the IN Cell Analyzer 1000 Optical Imaging System as described above. The results were analysed using an object intensity algorithm (IN Cell Investigator software).

5. EGFP NFAT Assay Using Genetically Engineered Cells 5.1 NFAT Proteins

The nuclear factor of activated T cells (NFAT) proteins are transcription factors whose activation is controlled by the $Ca^{2+}$/calmodulin-dependent phosphatase, calcineurin. NFAT signalling is involved in many processes including lymphocyte development and activation, skeletal muscle gene expression, remodelling and development and function of the cardiovascular system. Five different NFAT genes have been identified so far; NFATc (NFATc1 or NFAT2), NFATp (NFATc2 or NFAT1), NFAT4 (NFATc3 or NFATx), NFAT3 (NFATc4) and NFAT5.

The NFATc1 subtype is activated by antigen signalling in T cells resulting in cytokine expression but has also been shown to be involved in morphogenesis of the mammalian heart.

The upstream receptor-ligand interactions that lead to activation of NFATs are not well characterised in most cell types. However, members of the NFATc (cytoplasmic) family of proteins (NFATc1-c4) can be activated by various GPCRs that activate PLC and induce $IP_3$-mediated transient release of calcium from intracellular stores. In most cell-types, additional calcium influx through specialised calcium release activated calcium (CRAC) channels is required for activation of NFATc target genes. $IP_3$ can also spread through GAP junctions and activate CRAC channels and NFATc target genes in neighbouring cells.

A second pathway resulting in the activation of NFATs exist in some cell types such as mast cells. FcεR1 activation of mast cells is mediated by calcineurin controlled signalling pathways acting in synergy with the pathways regulated by GTPases of the Ras superfamily, Ras and Rac-1.

Inactive NFATc resides in the cytosol. It is phosphorylated at serine residues, which masks its nuclear localisation sequence (NLS) and presents its nuclear export sequence (NES). In response to sustained elevated calcium levels, NFATc is dephosphorylated by calcineurin, which exposes its NLS and it rapidly translocates to the nucleus. In the nucleus, it forms transcription complexes with other transcription factors such as AP-1, GATA4, GATA2 and MEF2. If calcium levels drop, NFATc is rephosphorylated, exposes the NES and the protein is exported back to the cytoplasm.

NFATc dephosphorylation and nuclear translocation can be inhibited by both cellular and pharmacological products. Four cellular inhibitors of calcineurin phosphatase complexes have been identified; scaffold protein AKAP79, CAIN or CABIN protein, calcineurin B homologue, CHP and the Down Syndrome Critical Region 1 related genes; MCIP1, 2 and 3. The microbial products, FK506 and Cyclosporine-A binds to the intracellular proteins, FKBP and Cyclophilin, respectively, and, subsequently binds to calcineurin and block phosphatase activity. These agents revolutionised transplant therapy because of their ability to prevent the immune response to transplanted tissue. Various kinases have been implicated in the negative regulation of NFATs including the GSK3, casein kinase 1, MEKK-1 and p38 MAPKs.

5.2 EGFP-NFAT assay

The present patent specification describes a method for monitoring the NFATC1 signalling pathway with a cell-secreted, cell-associated analyte. The assay method is based on the intracellular translocation of an EGFP-NFATc1 fusion protein in stably transfected mammalian cells. NFATc1 is a transcription factor involved in T-cell signalling and tissue development. Inactive NFATc1 transcription factors reside in the cytoplasm. Following activation with agonists these translocate to the nucleus.

The NFAT assay is optimised for image acquisition and analysis on the IN Cell Analysis System (GE Healthcare) using the Nuclear Trafficking-Analysis Module, although the assay can be imaged on other systems. The Nuclear Trafficking-Analysis Module measures the degree of EGFP-NFAT translocation from the cytoplasm to the nucleus on the addition of agonists.

5.3 U-2OS Derived Parental Cell Line

The parental cell line U-2OS (ATCC HTB-96) was derived from a moderately differentiated sarcoma of the tibia of a 15 year old girl. The U-2OS cell line is chromosomally highly alerted, with chromosome counts in the hypertriploid range, and expresses the insulin-like growth factor I and II receptors.

5.4 U-2OS Derived EGFP-NFATc1 Expressing Cell Line

U-2OS cells were transfected with the pCORON1000 EGFP-NFATc1 vector (GE Healthcare) using the FUGENE® 6 transfection method (Roche Applied Science) according to the manufacturers instructions. A stable clone expressing the recombinant fusion protein was selected using 500 µg/ml GENETICIN® for approximately 2 weeks. The stable cell line was cloned and sorted using a fluorescence activated cell sorter machine to obtain a uniform cell line. The passage number was set to one after FACS. Following sorting, the cells were grown for a further 8 passages before freezing. The cells tested were negative for mycoplasma, bacterial and yeast contamination.

5.5 EGFP-NFATc1 Expressing Vector

The 8.6 kb pCORON1000-EGFP-NFATc1, contains a bacterial ampicillin resistance gene and a mammalian neomycin resistance gene.

5.6 Material and Equipment Required

Microplates. For analysis using IN Cell, Packard Black 96-well VIEWPLATE™ (Perkin Elmer 6005182) were used. A CASY® 1 Cell Counter and Analyser System (Model TT) (Scharfe System GmbH) is recommended to ensure accurate cell counting prior to seeding. Alternatively a haemocytometer may be used.

Environmentally controlled incubator (5% $CO_2$, 95% relative humidity, 37° C.).

Imager (e.g. IN Cell Analyzer 1000 GE Healthcare).

Laminar flow cell culture bench.

Tissue culture flasks (T-flasks) and pipettes.

Controlled freezing rate device providing a controlled freezing rate of 1° C. per min.

Standard tissue culture reagents and facilities.

5.6.1 Software Requirements

IN Cell Analysis System: The Nuclear Trafficking-Analysis Module is available from GE Healthcare for automated image analysis of the EGFP-NFAT assay. Analysed data are exported as numerical files in an ASCII format. ASCII format data can be imported into Microsoft Excel, Microsoft Access or any similar package for further data analysis.

Culture and maintenance of U-2OS derived EGFP-NFATc1 expressing cell line.

5.6.2 Tissue Culture Media and Reagents Required

The following media and buffers are required to culture, maintain and prepare the cells, and to perform the assay.

GIBCO® Dulbecco's Modified EAGLE MEDIA (DMEM) with GLUTAMAX™-1,

Invitrogen Life Technologies 31966-021 or equivalent.

Foetal Bovine Serum (FBS), JRH Biosciences 12103 or equivalent. Heat inactivate serum by incubation in a water bath at 56° C. for 30 minutes.

GIBCO® Penicillin-Streptomycin (P/S), (5000 units/ml penicillin G sodium and 5000 µg/ml streptomycin sulphate) Invitrogen Life Technologies 15140-122 or equivalent.

GENETICIN® (G418), Sigma G-7034 or equivalent.

GIBCO® Trypsin-EDTA in HBSS without calcium or magnesium, Invitrogen Life

Technologies 25300-054 or equivalent.

GIBCO® HEPES buffer, 1M solution, Invitrogen Life Technologies 15630-056 or equivalent Bovine serum albumin (BSA), Sigma A-7888 or equivalent.

GIBCO® Phosphate Buffered Saline (PBS) Dulbecco's without calcium, magnesium or sodium bicarbonate, Invitrogen Life Technologies 14190-094 or equivalent.

Dimethylsulphoxide (DMSO), Sigma D-5879 or equivalent.

GIBCO® Nutrient Mixture F-12 medium with GLUTAMAX™, Invitrogen Life

Technologies 31765-027 or equivalent.

Ionomycin, calcium salt, Calbiochem, 407952

Hoechst 33258, Molecular Probes H-3569

5.6.3 Reagent Preparation

Growth-medium: DMEM with GLUTAMAX™-1 supplemented with 10% (v/v) FBS, 1% (v/v) Penicillin-Streptomyccin, and 0.5 mg/ml GENETICIN®.

Freeze-medium: DMEM with GLUTAMAX™-1 supplemented with 10% (v/v) FBS, 1% (v/v) Penicillin-Streptomycin and 10% (v/v) DMSO.

Assay-medium: Nutrient Mixture F-12 medium with GLUTAMAX™ supplemeted with 10 mM HEPES, 0.5% (w/v) BSA and 3.0 µM Hoechst Nuclear Stain.

Ionomycin: Prepare a 1 mM stock in 100% DMSO. This can be stored at −20° C. Prepare a 4 µM working dilution with assay-medium (four fold of the final concentration). This results in a final concentration of DMSO in the assay of 0.1% (v/v). 0.4% (v/v) DMSO (four fold of the final concentration) should be prepared in Assay-medium for control wells.

5.6.4 Cell Thawing Procedure

1. Remove a Cryo-Vial from Storage.
2. Holding the cryo-vial, dip the bottom three-quarters of the cryo-vial into a 37° C. water bath, and swirl gently 1-2 minutes until the contents are thawed.
3. Remove the cryo-vial from the water bath and wipe it with 70% (v/v) ethanol. Transfer the cells immediately to a T-25 flask and add 5 ml pre-warmed Growth-medium drop wise to prevent cell damage. Add a further 2 ml Growth-medium and incubate at 37° C.

5.6.5 Cell Subculturing Procedure

Incubation: 5% $CO_2$, 95% humidity, 37° C.

The cells should be split at a ratio of 1:10, two or three times a week, when they are 90% confluent.

1. Warm all reagents to 37° C.
2. Aspirate the medium from the cells and discard.
3. Wash the cells with PBS, taking care not to damage the cell layer while washing, but ensure the that the cell surface is washed.
4. Aspirate the PBS from the cells and discard.
5. Add trypsin-EDTA (2 ml for T-75 flasks and 4 ml for T-162 flasks) ensuring that all cells are in contact with the solution. Wait for 3-10 minutes for the cells to round up/loosen.
6. When the cells are loose, tap the flask gently to dislodge the cells. Add Growth-medium (6 ml for T-75 and 8 ml for T-162 flasks) and gently resuspend the cells with a 10 ml pipette until all the clumps have dispersed.
7. Aspirate the cell suspension and dispense 1 ml cells into a new culture vessel.

5.6.6 Cell Seeding Procedure

1. The following procedure is optimised for cells grown in standard T-75 and T-162 flasks to be seeded into 96-well microplates.
2. Warm all reagents to 37° C.
3. Aspirate the medium from the cells and discard.
4. Wash the cells with PBS. Take care not to damage the cell layer while washing, but ensure that the entire cell surface is washed.
5. Aspirate the PBS from the cells and discard.
6. Add Trypsin-EDTA (2 ml for T-75 and 4 ml for T-162 flasks), ensuring that all cells are in contact with the solution. Wait for 3-10 minutes for the cells to round up/loosen.
7. When the cells are loose, tap the flask gently to dislodge the cells. Add growth-medium (3 ml for T-75 and 6 ml for T-162 flasks) and gently resuspend the cells with a 10 ml pipette until all the clumps have dispersed.
8. Count the cells using an automated cell counter or a haemocytometer.
9. Using fresh Growth-medium, adjust the cell density to deliver the desired number of cells to each well. For example, to add $1.0 \times 10^4$ cells per well in a volume of 200 µl, adjust the suspension to $5 \times 10^4$ cells per ml.
10. Dispense 200 µl of the cells into each well of the microplate.
11. Incubate the plated cells for 24 h at 37° C. before starting the assay.

5.6.7 Cell Freezing Procedure
1. Harvest and count the cells.
2. Centrifuge the cells at 300×g for 5 minutes. Aspirate the medium from the cells.
3. Gently resuspend the cells until no clumps remain in freeze medium at a concentration of $1 \times 10^6$ cells in 1 ml and transfer into cryo-vials. Each vial should contain $1 \times 10^6$ cells in 1 ml of freeze medium.
4. Transfer the vials to a cryo-freezing device and freeze at −80° C. for 16-24 h.
5. Transfer the vials to the vapour phase in a liquid nitrogen storage device.

5.6.8 Growth Characteristics
Under standard growth conditions, the cells should maintain an average size of 18.5 µM as measured using a CASY® Cell Counter and Analyzer System (Model TT). The doubling time of the cell line in an exponential growth phase is 14 hours under standard conditions.

5.6.9 Agonist Assay Protocol (96-Well Format)
1. Incubate the microplate at 37° C., 5% $CO_2$ and 95% humidity.
2. The day before commencing the assay, seed at $1 \times 10^4$ cells per well in 200 µl of growth medium. Incubate for 24 hours at 37° C. If one of the wells on the cell plate is used for flat field correction, it should not contain cells.
3. On the day of the assay, prepare the test compounds, solvent controls (if used) and reference agonist control (Ionomycin). These samples were typically prepared at four fold of the final concentration in assay medium.
4. The growth medium from the cell plate was decanted, removing all excess liquid and add 200 µl. Using cell culture medium, wash the cells. Decant the wash.
5. Add 150 µl assay medium containing test agent. Incubate for 60 minutes.
6. The total volume is 200 µl. After the suitable incubation period, image the plate on the IN Cell Analyzer 1000 using appropriate filters and dichroic mirror.
7. Carry out the data analysis using the Nuclear Trafficking Analysis module.

6. CHO-M1 Nitroreductase Gene Reporter Assay Using Genetically Engineered Cells 6.1 Introduction
Reporter gene assay technology is widely used to monitor the cellular events associated with signal transduction and gene expression. The term reporter gene is used to define a gene with a readily measurable phenotype that can be distinguished easily over a background of endogenous proteins. A reporter gene construct is comprised of an inducible transcriptional control element driving the expression of a reporter gene.

Generally, such reporters are selected on the basis of the sensitivity, dynamic range, convenience and reliability of the assay.

Nitroreductase (NTR) is an FMN-dependent enzyme isolated from *Escherichia coli* B. NTR is one member of a structurally homologous family, containing four flavoproteins whose crystal structures have been solved. This family can be divided into two groups, nitroreductases, of which NTR is a member and flavin reductases such as FRase 1. The nitroreductase can be further sub-divided into two classes; oxygen sensitive and insensitive. The NTR described in this system belongs to the oxygen insensitive class of enzymes. The structure of NTR consists of a homodimers of 48 kDa with two molecules of FMN bound which is capable of reducing a number of nitro-containing compounds. Expression of NTR has been demonstrated in a number of mammalian cells without any reported toxicity. The ability of this enzyme to reduce nitro groups, a common mechanism for quenching the fluorescence of molecules has led to the development of a convenient gene reporter assay system based on the expression of NTR and a cell permeable quenched cyanine dye-CYTOCY5S™. CYTOCY5S™ is membrane permeant and acts as a substrate for the enzyme permitting the use of NTR as a reporter of gene expression in living mammalian cells. The substrate has been optimised to improve the cellular retention of the reaction product. Typically current reporter gene systems available are invasive and require destruction of the cell in order to measure gene reporter expression (firefly luciferase) or have limited sensitivity (GFP) due to the absence of enzymatic amplification. To overcome these limitations the NTR gene reporter system has been developed as a non-invasive live cell reporter system that uses a cell permeable fluorogenic substrate. Analysis of NTR gene reporter assays on the IN Cell Analyzer 1000 allows visualisation of gene expression in single living cells. The NTR gene reporter system is simple and convenient to use.

6.2 Transfection Methods
To establish a reporter gene assay, the reporter gene is placed under the transcriptional control of a promoter or an enhancer with a minimal promoter. The promoter plus reporter gene is inserted into a suitable vector such as a plasmid containing a selectable marker that confers resistance to growth suppressing compounds, such as antibiotics e.g. neomycin. The reporter DNA is introduced into cells to provide either a transient assay or stably integrated into the genome of the host cell line to provide a stable reporter cell line. Introduction of the plasmid construct into mammalian cells is termed transfection and there are many commercially available reagents for delivering DNA into cells, such examples include liposomes, calcium phosphate and dendrimer technologies. Transient transfection with plasmids is a very versatile and easy to carry out technique. Transient transfections are generally performed overnight and allow the researcher to do single "one-off" experiments that will provide information on the functionality of the vector DNA. The vector DNA molecule does not integrate into the host chromatin but exists as an extrachromosomal molecule with a lifetime of typically 24-96 hours after which the DNA and expression of the reporter gene are lost. One major limitation with transient transfections is the variation in transfection efficiency, which can produce a heterogeneous population of cells and poor results if internal controls are not included.

Stable transfection will provide a cell line which contains the reporter gene plus a selection marker integrated into the host genome, i.e. an inheritable genotype.

6.3 Production of Stable and Transiently Transfected Cell Lines
6.3.1 Transient Transfection
6.3.1.1 Method-Plasmid Based Transfection
1. Seed cells into sterile 60 mm tissue culture treated Petri dishes. Incubate the dishes overnight at 37° C.

2. When the cells attain 50-70% confluence, replace the medium with 3 ml of fresh growth medium.
3. Add reporter DNA/transfection reagent complex to each dish (ratio of DNA to transfection agent prepared and optimised according to suppliers instructions). Incubate overnight at 37° C.
4. After overnight incubation, remove the medium from each dish (ratio of DNA to transfection agent prepared and optimized according to suppliers instructions). Incubate overnight at 37° C.
5. After overnight incubation, remove the medium from each dish and wash cell monolayers with 3 ml phosphate buffered saline (PBS). Trypsinise and pool cells from each dish to produce a suspension of transfected cells.

6.3.2 Stable Transfection

The process of establishing stable cell lines involves a large number of variables, many of which are cell-line dependent. Standard methods and guidelines for the generation of cell lines can be found in: Freshney R.I. Cloning and Selection of Specific Cell Types in Culture of Animal Cells, 3rd edition, Wiley-Liss Inc, Chapter 11, pp 161-178, 1994. Briefly, for stable cell line production, selection with G418 for pCORON-1003NFAT-NTR vector or hygromycin for pCORON5023NFAT-NTR vector is necessary. 24-48 hours post-transfection the cells should be placed under selection with the appropriate concentration of antibiotic.

Once sufficient cells have grown, they should be seeded at a low density into a suitable dish or plate in medium containing selection antibiotic.

The optimal concentration of selection antibiotic will vary according to the cell type and growth rate and users should perform a death curve on the host cells prior to transfection. The media containing the selection antibiotic should be changed twice a week, until drug-resistant colonies appear. This may take between 2 and 6 weeks depending on cell type. A negative control of non-transfected cells should be included to determine the effectiveness of the selection procedure. Death of the control cells should be observed between 3-10 days following selection. Single colonies should be selected and expanded to create a library of cell lines. The individual clonal cell lines should be screened for correct biological response and optimal assay performance based on the user criteria.

6.4 Cell Culture of CHO-M1 NFAT-NTR Cell Line
6.4.1 Cell Thawing Procedure
Remove a cryo-vial from storage.
Holding the cryo-vial, dip the bottom three-quarters of the cryo-vial into a 37° C. water bath, and swirl gently for 1-2 minutes until the contents are thawed. Do not thaw the cells for longer than 3 minutes as this decreases viability.
Remove the cryo-vial from the water bath and wipe it with 70% (v/v) ethanol. Transfer the cells immediately to a T-flask containing growth medium at 37° C.

CHO-M1 NFAT-NTR cells are routinely passaged 1:10 in Ham's F12 medium supplemented with 10% foetal calf serum, 2 mM L-glutamine, 100 units/ml penicillin and 100 µg/ml streptomycin. Selection is maintained with 0.5 mg/ml Neomycin (G418) and 0.25 mg/ml Hygromycin. The cells are grown as monolayers in 162 cm2 tissue-culture treated flasks and incubated at 37° C. in an atmosphere containing 5% $CO_2$. On removal of the cells from cryopreservation, it is recommended that 0.5 mg/ml G-418 and 0.25 mg/ml Hygromycin is omitted until the cells have adhered to the flask, typically overnight. Once cells are established in culture, selection should be maintained with 0.5 mg/ml G-418 and 0.25 mg/ml Hygromycin.

6.4.2 Assay Protocol

A reporter plasmid was constructed containing the 4 repeats of the NFAT response element upstream of the NTR gene. The plasmid was introduced into CHO-M1 cells and maintained under dual selection until clones were obtained. Single clones were isolated using limited dilution, propagated and assessed for biological response.

6.5 Reagent Preparation
6.5.1 Phosphate Buffered Saline
GIBCO®BRL 14190-094 Alternative formulations and commercially available concentrates etc may be used.
6.5.2 CYTOCY5S™ Solution
Reconstitute with DMSO to a concentration 0 f 1-5 mM. Further dilutions should be made in assay buffer to give a solution (typically 5-10 µM) which is added to the cells usually as a 10× stock to give final concentrations required.
6.5.3 Carbachol
Sigma C4382-1 g
Prepare a 100 mM stock solution in PBS. Vortex to resuspend the contents. Dilute the required concentration in assay medium.
6.5.4 Hoechst Reagent
If nuclear staining is required for image analysis, prepare a stock of Hoechst solution in assay buffer. Prepare Hoechst at 25 µM in phenol red/serum free medium and add 10 µl per well. For imaging plates on the IN Cell Analyzer 1000, a suitable cell marker should be introduced into the cell. An example is the nuclear marker Hoechst. This label should be bright enough to permit identification of the cell as an object during analysis and spectrally separated from the CYTOCY5S™ so as not to interfere with the signal. Typically concentrations between 2.5-5 µM are used for Hoechst.
6.5.5 Controls for Transient Assays
6.5.5.1 Non-Transfected Control
This should be included in each experiment. The non-transfected control provides information on any background level of fluorescence and is a check to ensure there is no NTR-like activity present in the host cell line. Assays should be carried out with and without agonist.
6.5.5.2 Non-Stimulated Control
The non-stimulated control provides information on the baseline expression of the NTR gene under the control of the NFAT response element in the cell line chosen. The value from this control may vary with different cell lines and with assay set-up conditions.
6.6 Example 96-Well Assay Protocol
Prepare CHO-M1 NFAT-NTR cells at $2.5 \times 10^5$ cells per ml in complete Ham's F12 medium containing 2 mM L-glutamine and 10% FCS (without selection agents). Dispense 200 µl ($5 \times 10^4$ cells) into each well of a 96-well microplate. Incubate plates overnight at 37° C.

1. Following overnight incubation remove medium and wash cell monolayers with 200 µl PBS.
2. Add 90 µl agonist (e.g. carbachol) in assay medium to appropriate wells, and, 90 µl assay medium to control wells. Incubate plates at 37° C. for 16 hours.
3. After the 16 hour incubation, dispense 10 µl 10 µM CYTOCY5S™ in assay medium (final concentration is typically 0.5 µM-1 µM).
4. Incubate at 37° C. for a further 2 hours.
5. Add 10 µl of 25 µM Hoechst nuclear dye in phenol red/serum-free medium. Incubate for 30 minutes at room temperature.
6. Image plates. Use appropriate filters for CYTOCY5S™ (excitation filter 620/60 nm; emission filter 700/75 nm). Assays were imaged on the IN Cell Analyzer 1000 using the Object Intensity Algorithm.

7. ELISPOT Assays for the Measurement of Secreted/Cell-Associated Analyte

7.1 Introduction

The Elispot (Enzyme Linked Immuno-Spot) assay provides an effective method of measuring antibody or cytokine production from cells at the single cell level or at very low cell numbers.

7.2 Reagents

1. Anti-TNF antibodies (Sigma)
2. ELISPOT Plate (Millipore HTS cat number MSIPS4510)
3. Ionomycin or carbachol (Sigma)
4. Biotinylated anti-TNF antibodies (R&D Systems)

7.3 Method

Day 1
1. Coat ELISPOT plate (Millipore HTS cat number MSIPS4510) with primary antibody (see below).
2. Pre-wet each well with 15 µl of 35% ethanol for one minute. Rinse with 150 µl sterile PBS three times before the ethanol evaporates.
3. Coat plates with 100 µl (10 µg/ml) (for example) anti-TNF antibodies in sterile PBS. Incubate overnight at 4° C.
4. The following control wells were incorporated into the assay.
5. No cells
6. No primary antibody
7. No test-agent stimulation Day 2
1. Block membrane
2. Decant primary antibody solution.
3. Wash off unbound antibody with 150 µl sterile PBS per well; decant wash and repeat.
4. Block membrane with 150 µl per well of cell medium (RPMI-1640, 10% foetal calf serum, 1% non-essential amino acids, penicillin, streptomycin, glutamine) for at least 2 hours at 37° C.
5. Prepare cells (e.g. wild-type U-2OS (ECAAC), or, U-2OS derived cell line expressing EGFP-NFATc1 fusion protein (GE Healthcare), or, Chinese Hamster Ovary (CHO) NFAT-NTR cells (GE Healthcare).
6. Wash cells in sterile PBS and resuspend cells at a final concentration of $2.5 \times 10^5$ cells/ml in cell medium.
7. Stimulate the cells with the test agent (for example ionomycin or carbachol).
8. Plate out cells.
9. Decant blocking medium from the ELISPOT plate.
10. Add cells in 100 µl cell medium per well.
11. Incubate for 18 to 48 hours at 37° C., 5% $CO_2$ and 95% humidity.

Day 3
1. Decant cells.
2. Wash plate 6 times with PBS/0.01% TWEEN™ 20. A squeeze bottle can be utilized to ensure adequate washing.
3. Dilute biotinylated anti-TNF antibodies to 2 µg/ml in PBS/0.5% BSA. Filter through a 0.45 µM filter. Add 100 µl/well.
4. Incubate for 2 hours at 37° C., 5% $CO_2$, and 95% humidity.
5. Wash 6 times with PBS/0.01% TWEEN™ 20.
6. Prepare streptavidin-alkaline phosphatase enzyme conjugate at 1:1000 in sterile PBS.
7. Add 100 µl per well of streptavidin-alkaline phosphatase. Incubate for 45 minutes at room temperature.
8. Decant streptavidin, wash 3 times with PBS/0.01% TWEEN™ 20, followed by 3 washes with PBS.
9. Add 100 µl/well BCIP/NBT plus substrate. Incubate for 5 minutes.
10. Stop spot development under running water and wash extensively. While washing, remove underplate plate seal and continue rinsing.
11. Blot plate to remove excess liquid and dry back of wells with an absorbent wipe. This will ensure that the substrate has been completely removed from the membrane.
12. Capture cellular/spot images immediately, or, alternatively, let the ELISPOT plate dry overnight in the dark.
13. Analyze plate using IN Cell Imaging System using bright field settings.

8. Combination Assay of Human TNF, IL-8, or PDGF from Ionomycin, Ionomycin+PMA or Calcium Ionophore A23187 Stimulated EGFP-NFATc1, Using EGFP Translocation Assay and Transfected U-2OS Cells on IN Cell Analyzer 1000

8.1 Materials

Rabbit anti-human TNF or rabbit anti-human IL-8 antibodies (Sigma)

Anti-rabbit anti-PDGF-A (N-30) antibodies (Santa Cruz Biotechnology, sc-128).

Anti-rabbit IgG (whole molecule) R-Phycoerythrin conjugate (Sigma; P9537).

Anti-rabbit IgG (whole molecule) fluorescein conjugate (GE Healthcare; N1034).

Ionomycin (Sigma; 13909).

Calcium ionophore A23187 (Sigma) C7522.

PMA Sigma (P1585).

8.2 Method

1. The day before commencing the assay, seed EGFP-NFATc1 transfected U2OS cells at $1 \times 10^4$ cellsper well in 200 µl of growth medium.
2. On the day of the assay, prepare the test agent (ionomycin, ionomycin+PMA, A23187). These samples are typically prepared in assay medium.
3. Decant the growth medium from the cell plate, removing all excess liquid and add 200 µl. Using the cell culture medium, wash the cells. Decant the wash.
4. Add 150 µl assay medium containing test agent. Incubate for 60 minutes.
5. The total volume is 200 µl. After the suitable incubation period, image the plate on the IN Cell Analyzer 1000 using appropriate filters and dichroic mirror.
6. Carry out the data analysis using the Nuclear Trafficking Analysis module.
7. Cells were contacted with test agent for a further 3-18 hours and cell associated TNF, IL-8 or PDGF was measured post stimulation with test agent.
8. After stimulation with the test agent, the supernatant was decanted and the cells were washed ×3 with PBS. Cell-associated TNF, IL-8 or PDGF was localised with an anti-human TNF, IL-8 or PDGF antibody and a fluorescent dye-labelled anti-rabbit IgG (anti-rabbit IgG (whole molecule) R-Phycoerythrin conjugate (Sigma; P9537), or, anti-rabbit IgG (whole molecule) fluorescein conjugate (GE Healthcare; N1034).
9. After 60 minutes incubation with the rabbit antibody, the cells were washed ×3 and the dye labelled anti-rabbit IgG added. After 60 minutes incubation with the fluor-labelled second antibody, the cell were washed ×3 with PBS, and fluorescence detected on an IN Cell Analyzer 1000 (GE Healthcare), using a 10× objective, suitable filter set and dichroic, 500 ms exposure. The results were analysed using an object intensity algorithm (IN Cell Investigator software).

Figure 11:
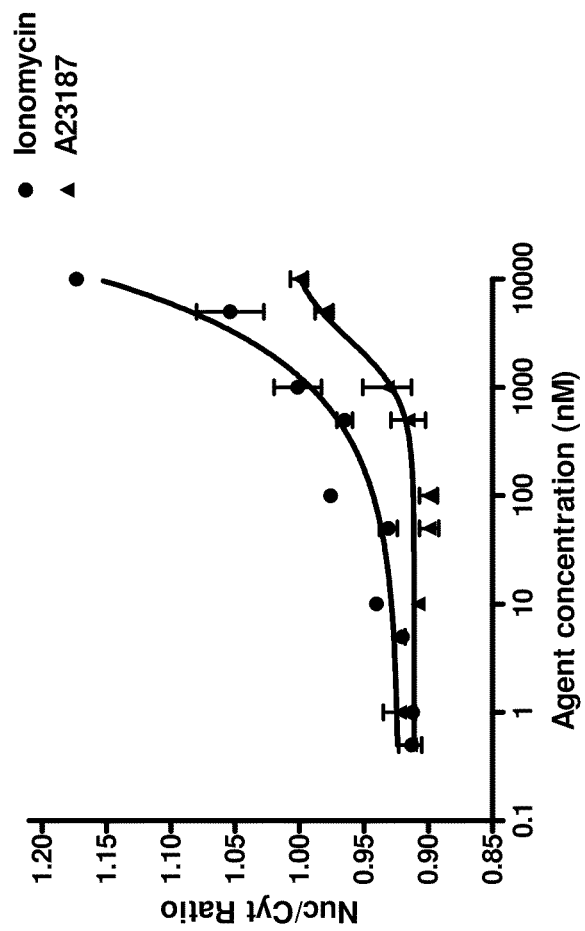
FIG. 11 shows EGFP-NFAT1c translocation from the combination assay of EGFP translocation and PDGF measurement (cell-associated molecule).

FIG. 11 shows EGFP-NFAT1c translocation from the combination assay of EGFP translocation and PDGF measurement (cell-associated molecule). Transfected U2OS cells were stimulated with ionomycin or calcium ionophore A23187 resulting in the EGFP-NFAT1c cell response measured on IN Cell Analyzer 1000.

Figure 12:
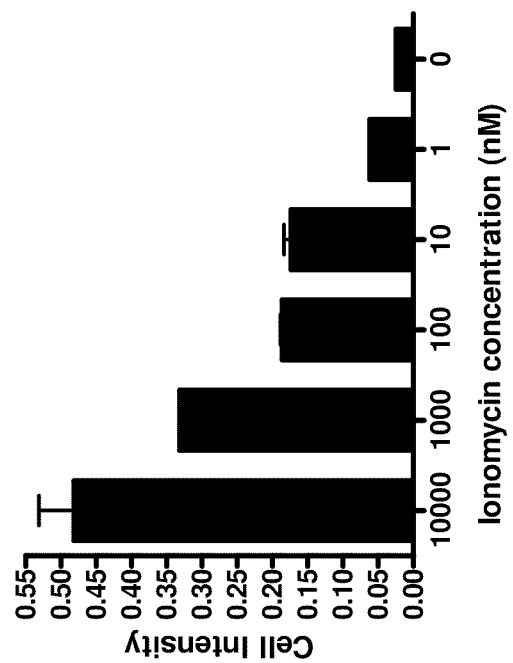
FIG. 12 shows ionomycin-stimulated PDGF release from EGFP-NFAT1c transfected U2OS cells in combination with EGFP-NFAT1c translocation.

FIG. 12 shows ionomycin-stimulated PDGF release from EGFP-NFAT 1c transfected U2OS cells in combination with EGFP-NFAT1c translocation (FIG. 11).

Figure 13:
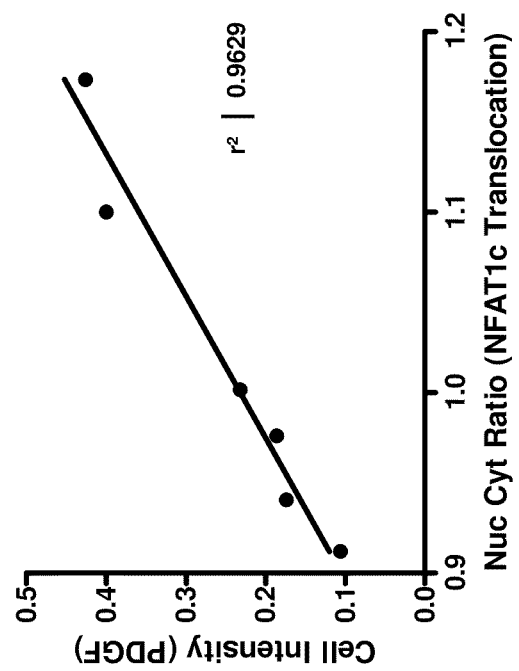
FIG. 13 shows a correlation between intracellular NFAT1c translocation and cell-associated PDGF from ionomycin-stimulated EGFP-NFAT1c transfected U2OS cells from a single population.

FIG. 13 shows a correlation between intracellular NFAT1c translocation and cell-associated PDGF from ionomycin-stimulated EGFP-NFAT1c transfected U2OS cells from a single population (correlation coefficient 0.9629). Results were obtained on the IN Cell Analyzer Optical Imaging System as described above.

Figure 14:
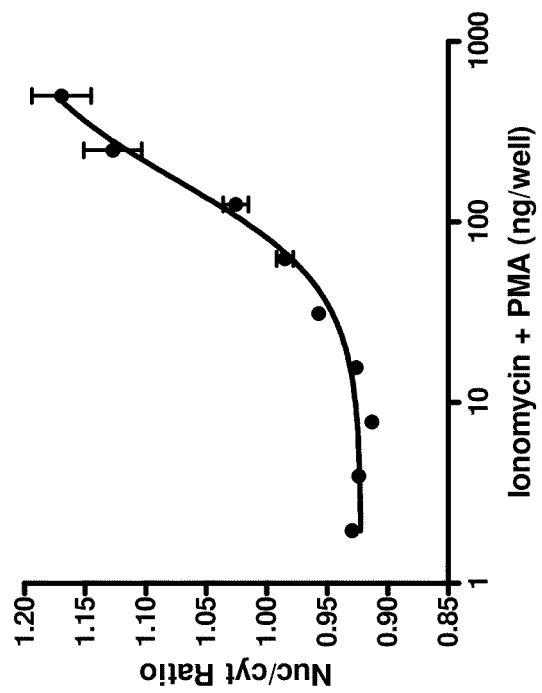
FIG. 14 shows EGFP-NFAT1c translocation upon stimulation of transfected cells with ionomycin+PMA as measured using an imaging system.

FIG. 14 shows EGFP-NFAT1c translocation upon stimulation of transfected cells with ionomycin+PMA as measured on the IN Cell Analyzer 1000 Optical Imaging System.

Figure 15:
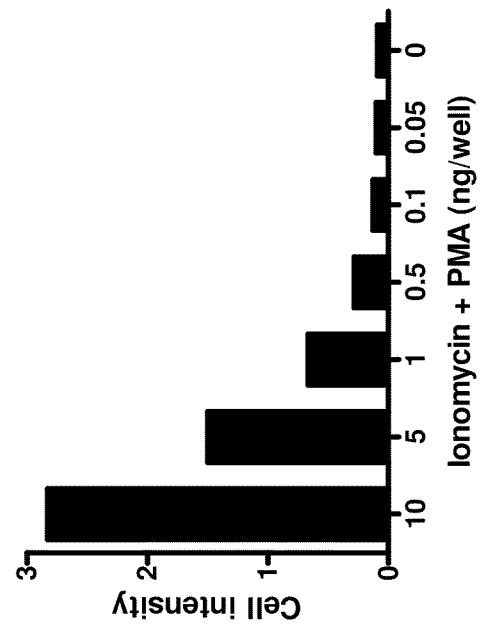
FIG. 15 shows ionomycin+PMA stimulated TNFα release from EGFP-NFAT1c transfected U2OS cells obtained in combination with EGFP-NFAT1c translocation.

FIG. 15 shows ionomycin+PMA stimulated TNFα release from EGFP-NFAT1c transfected U2OS cells obtained in combination with EGFP-NFAT1c translocation (FIG. 14).

Figure 16:
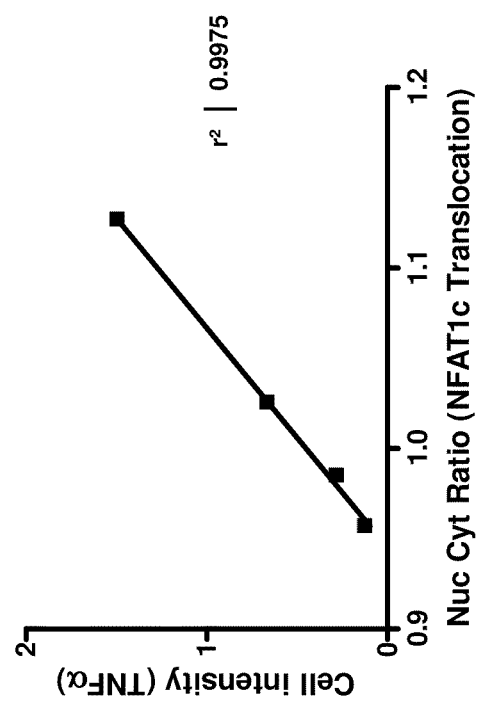
FIG. 16 shows a correlation between intracellular NFAT1c translocation and cell-associated human TNFα from ionomycin+PMA-stimulated EGFP-NFAT1c transfected U2OS cells.

FIG. 16 shows a correlation between intracellular NFAT1c translocation and cell-associated human TNFα from ionomycin+PMA-stimulated EGFP-NFAT1c transfected U2OS cells from a single population (correlation coefficient 0.9975). Results were obtained on the IN Cell Analyzer Optical Imaging System as described above.

9. Combination Assay of Human TNF Using ELISPOT Assay for Cell-Associated Analyte and EGFP Translocation, from Ionomycin+PMA Stimulated EGFP-NFATc1 Transfected U2OS Cells on IN Cell Analyzer 1000

9.1 Reagents
1. Anti-TNF antibodies (Sigma)
2. ELISPOT Plate (Millipore HTS cat number MSIPS4510)
3. Ionomycin or carbachol (Sigma)
4. Biotinylated anti-TNF antibodies (R&D Systems)

9.2 Method
1. Coat ELISPOT plate (Millipore HTS cat number MSIPS4510) with primary antibody.
2. Pre-wet each well with 15 μl of 35% ethanol for one minute. Rinse with 150 μl sterile PBS three times before the ethanol evaporates.
3. Coat plates with 100 μl (10 μg/ml) (for example) anti-TNF antibodies in sterile PBS. Incubate overnight at 4° C.
4. The following control wells were incorporated into the assay.
5. No cells
6. No primary antibody
7. No test agent stimulation
8. Decant primary antibody solution.
9. Wash off unbound antibody with 150 μl sterile PBS per well; decant wash and repeat.
10. Block membrane with 150 μl per well of cell medium (RPMI-1640, 10% foetal calf serum, 1% non-essential amino acids, penicillin, streptomycin, glutamine) for at least 2 hours at 37° C. Decant blocking medium from the ELISPOT plate.
11. Prepare cells (a cell line expressing EGFP-NFATc1 fusion protein (GE Healthcare), Wash cells in sterile PBS and resuspend cells at a final concentration of 2.5× $10^5$ cells/ml in cell medium.
12. Plate out cells in 100 μl cell medium per well.
13. Stimulate the cells with the test agent (e.g. ionomycin+PMA).
14. The total volume is 200 μl.
15. Incubate for 60 minutes. Add Hoescht stain to a final concentration of 1 μM.
16. Wash cells with assay medium.
17. Carry out cellular analysis on IN Cell Analyzer 1000 using the Nuclear Trafficking Analysis Module.
18. Incubate cell in assay medium for a further 18 to 48 hours at 37° C., 5% $CO_2$ and 95% humidity.
19. Decant cells.
20. Wash plate 6 times with PBS/0.01% TWEEN™ 20. A squeeze bottle can be utilized to ensure adequate washing.
21. Dilute biotinylated anti-TNF antibodies to 2 μg/ml in PBS/0.5% BSA. Filter through a 0.45 μM filter. Add 100 μl/well.
22. Incubate for 2 hours at 37° C., 5% $CO_2$, and 95% humidity.
23. Wash 6 times with PBS/0.01% TWEEN™ 20.
24. Prepare streptavidin-alkaline phosphatase enzyme conjugate at 1:1000 in sterile PBS.
25. Add 100 μl per well of streptavidin-alkaline phosphatase. Incubate for 45 minutes at room temperature.
26. Decant streptavidin, wash 3 times with PBS/0.01% TWEEN™ 20, followed by 3 washes with PBS.
27. Add 100 μl/well BCIP/NBT plus substrate. Incubate for 5 minutes.
28. Stop spot development under running water and wash extensively. While washing, remove underplate plate seal and continue rinsing.
29. Blot plate to remove excess liquid and dry back of wells with an absorbent wipe. This will ensure that the substrate has been completely removed from the membrane.
30. Let the plate dry overnight in the dark.
31. Analyze plate using IN Cell Analyzer 1000 Imaging System using bright field settings.

10. Combination assay of carbachol-stimulated CHO-M1 NFAT-NTR with measurement of NFAT1c-NTR intracellular reporter gene assay and human integrin 5 alpha (cell-associated analyte).

10.1 Reagents
Carbachol (Sigma)
CYTOCY5S™ (GE Healthcare)
Hoechst nuclear dye (Invitrogen)
Rabbit anti-hamster Integrin 5 antibody (Antibodies OnLine ABIN219718)
Fluorescein labelled anti-rabbit IgG (GE Healthcare)

10.2 Method
1. Prepare CHO-M1 NFAT-NTR cells at 2.5×$10^5$ cells per ml in complete Ham's F12 medium containing 2 mM L-glutamine and 10% FCS (without selection agents). Dispense 200 μl (5×$10^4$ cells) into each well of a 96-well microplate. Incubate plates overnight at 37° C.
2. Following overnight incubation remove medium and wash cell monolayers with 200 μl PBS.
3. Add 90 μl agonist (e.g. carbachol) in assay medium to appropriate wells, and, 90 μl assay medium to control wells. Incubate plates at 37° C. for 16 hours.
4. After the 16 hour incubation, dispense 10 μl 10 μM CYTOCY5S™ in assay medium (final concentration is typically 0.5 μM-1 μM).
5. Incubate at 37° C. for a further 2 hours.
6. Add 10 μl of 25 μM Hoechst nuclear dye in phenol red/serum-free medium. Incubate for 30 minutes at room temperature.
7. Image plates Use appropriate filters for CYTOCY5S™ (excitation filter 620/60 nm; emission filter 700/75 nm).

Assays were imaged on the IN Cell Analyzer 1000 using the Object Intensity Algorithm.

8. Incubate cells overnight at 37° C., 5% $CO_2$.

9. Cells were contacted with test agent for a further 18 hours and cell associated Integrin alpha 5 was measured post-stimulation with test agent. After stimulation with the test agent, the supernatant was decanted and the cells were washed ×3 with PBS. Cell-associated Integrin was localised with a rabbit anti-hamster Integrin 5 antibody and a fluorescent dye-labelled anti-rabbit IgG (whole molecule) fluorescein conjugate (GE Healthcare; N1034). 10. After 60 minutes incubation with the rabbit antibody, the cells were washed ×3 and the dye labelled anti-rabbit IgG added. After 60 minutes incubation with the fluor-labelled second antibody, the cell were washed ×3 with PBS, and fluorescence detected on an IN Cell Analyzer 1000 (GE Healthcare), using a 10× objective, suitable filter set and dichroic, 500 ms exposure. The results were analysed using an object intensity algorithm (IN Cell Investigator software).

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for measuring at least one intracellular event and a cell-surface associated analyte in a single population of living cells wherein said at least one intracellular event and said cell-surface associated analyte are each components of a concerted biochemical process operating in said cells, the method comprising the steps of:
   a) providing a sample containing a single population of living cells;
   b) contacting at least one living cell in said single population of cells with a test agent causing said at least one cell to produce a cell-surface associated analyte;
   c) measuring a change in a physical property in said at least one cell in step b) as a measure of at least one intracellular event;
   d) washing the cells to remove extracellular fluids;
   e) measuring the presence, amount or activity of said produced cell-surface associated analyte; and
   f) correlating the measured change in said at least one intracellular event in said at least one cell with the measured presence, amount or activity of said cell-surface associated analyte.

2. The method of claim 1, wherein in step a) each cell in said population of cells further comprises a reporter gene construct comprising a nucleic acid sequence encoding a detectable reporter molecule operably linked to and under the control of an expression control element; and wherein said contacting step b) is performed under conditions permitting expression of said reporter gene construct.

3. The method of claim 2, wherein said reporter gene construct comprises a nucleic acid sequence encoding a fluorescent protein.

4. The method of claim 3, wherein the fluorescent protein is a Green Fluorescent Protein (GFP) or a functional GFP analogue.

5. The method of claim 2, wherein said reporter gene construct comprises a nucleic acid sequence encoding an enzyme.

6. The method of claim 5, wherein said enzyme is selected from the group consisting of a luciferase, β-galactosidase, alkaline phosphatase and nitroreductase.

7. The method of claim 1, wherein said intracellular event is an increase in ion concentration and/or an increase in gene expression.

8. The method of claim 1, wherein in step c) said at least one intracellular event is measured by a change in fluorescence emitted by the cell.

9. The method of claim 1, wherein in step c) said at least one intracellular event is measured by an optical imaging method.

10. The method of claim 1, wherein the presence, amount or activity of said cell-surface associated analyte is measured by an immunochemical method.

11. The method of claim 1, wherein the presence, amount or activity of said cell-surface associated analyte is measured by an optical imaging method.

12. The method of claim 1, wherein the population of cells consists of mammalian cells.

13. The method of claim 1, wherein said test agent is a chemical entity selected from the group consisting of a drug, a food dye, a hormone, a toxin, an alkylating agent, an oxidising agent and a carcinogen.

14. The method of claim 1, wherein said test agent is a physical agent selected from the group consisting of electromagnetic radiation, β-radiation and heat.

* * * * *